(12) United States Patent
Levine et al.

(10) Patent No.: US 11,173,307 B2
(45) Date of Patent: Nov. 16, 2021

(54) VAGUS NERVE STIMULATION PRE-SCREENING TEST

(71) Applicant: SetPoint Medical Corporation, Valencia, CA (US)

(72) Inventors: Jacob A. Levine, West Hempstead, NY (US); Ralph J. Zitnik, Santa Barbara, CA (US)

(73) Assignee: SetPoint Medical Corporation, Valencia, CA (US)

( * ) Notice: Subject to any disclaimer, the term of this patent is extended or adjusted under 35 U.S.C. 154(b) by 253 days.

(21) Appl. No.: 16/103,873

(22) Filed: Aug. 14, 2018

(65) Prior Publication Data

US 2019/0046799 A1    Feb. 14, 2019

Related U.S. Application Data

(60) Provisional application No. 62/545,284, filed on Aug. 14, 2017.

(51) Int. Cl.
| | | |
|---|---|---|
| *A61N 1/36* | (2006.01) | |
| *G01N 33/68* | (2006.01) | |
| *A61N 1/372* | (2006.01) | |
| *A61N 7/00* | (2006.01) | |
| *A61N 2/00* | (2006.01) | |
| *A61N 1/04* | (2006.01) | |

(52) U.S. Cl.
CPC ..... *A61N 1/36053* (2013.01); *G01N 33/6863* (2013.01); *G01N 33/6869* (2013.01); *A61N 1/0456* (2013.01); *A61N 1/3606* (2013.01); *A61N 1/372* (2013.01); *A61N 2/006* (2013.01); *A61N 2007/0026* (2013.01); *G01N 2333/525* (2013.01); *G01N 2333/535* (2013.01); *G01N 2333/54* (2013.01); *G01N 2333/545* (2013.01); *G01N 2333/5412* (2013.01); *G01N 2333/5434* (2013.01); *G01N 2333/57* (2013.01); *G01N 2800/52* (2013.01); *G01N 2800/709* (2013.01); *G01N 2800/7095* (2013.01)

(58) Field of Classification Search
CPC .... A61N 1/05; A61N 1/0456; A61N 1/36053; G01N 33/6863
USPC ....................................................... 607/116
See application file for complete search history.

(56) References Cited

U.S. PATENT DOCUMENTS

| | | | |
|---|---|---|---|
| 2,164,121 | A | 6/1939 | Pescador |
| 3,363,623 | A | 1/1968 | Atwell |
| 3,631,534 | A | 12/1971 | Hirota et al. |

(Continued)

FOREIGN PATENT DOCUMENTS

| | | |
|---|---|---|
| CN | 201230913 A | 5/2009 |
| CN | 101528303 A | 9/2009 |

(Continued)

OTHER PUBLICATIONS

US 6,184,239 B1, 02/2001, Puskas (withdrawn)

(Continued)

*Primary Examiner* — Nadia A Mahmood
(74) *Attorney, Agent, or Firm* — Shay Glenn LLP

(57) ABSTRACT

Diagnostic screening tests that can be used to identify if a patient is a good candidates for an implantable vagus nerve stimulation device. One or more analyte, such as a cytokine or inflammatory molecule, can be measured from a blood sample taken prior to implantation of a vagus nerve stimulator to determine the patient's responsiveness to VNS for treatment of an inflammatory disorder.

12 Claims, 9 Drawing Sheets

(56) References Cited

U.S. PATENT DOCUMENTS

| | | |
|---|---|---|
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Iino et al. |
| 5,712,375 A | 1/1998 | Jensen et al. |
| 5,718,912 A | 2/1998 | Thompson et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,824,027 A | 10/1998 | Hoffer et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |

(56) References Cited

U.S. PATENT DOCUMENTS

| | | |
|---|---|---|
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,475 B1 | 5/2004 | Whitehurst et al. |
| 6,760,626 B1 | 7/2004 | Boveja |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,373,204 B2 | 5/2008 | Gelfand et al. |
| 7,389,145 B2 | 6/2008 | Kilgore et al. |
| 7,454,245 B2 | 11/2008 | Armstrong et al. |
| 7,467,016 B2 | 12/2008 | Colborn |
| 7,544,497 B2 | 6/2009 | Sinclair et al. |
| 7,561,918 B2 | 7/2009 | Armstrong et al. |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,060,208 B2 | 11/2011 | Kilgore et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,180,447 B2 | 5/2012 | Dacey et al. |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,391,970 B2 | 3/2013 | Tracey et al. |
| 8,412,338 B2 | 4/2013 | Faltys |
| 8,571,654 B2 | 10/2013 | Libbus et al. |
| 8,577,458 B1 | 11/2013 | Libbus et al. |
| 8,600,505 B2 | 12/2013 | Libbus et al. |
| 8,612,002 B2 | 12/2013 | Faltys et al. |
| 8,630,709 B2 | 1/2014 | Libbus et al. |
| 8,688,212 B2 | 4/2014 | Libbus et al. |
| 8,700,150 B2 | 4/2014 | Libbus et al. |
| 8,729,129 B2 | 5/2014 | Tracey et al. |
| 8,788,034 B2 | 7/2014 | Levine et al. |
| 8,843,210 B2 | 9/2014 | Simon et al. |
| 8,855,767 B2 | 10/2014 | Faltys et al. |
| 8,886,339 B2 | 11/2014 | Faltys et al. |
| 8,914,114 B2 | 12/2014 | Tracey et al. |
| 8,918,178 B2 | 12/2014 | Simon et al. |
| 8,918,191 B2 | 12/2014 | Libbus et al. |
| 8,923,964 B2 | 12/2014 | Libbus et al. |
| 8,983,628 B2 | 3/2015 | Simon et al. |
| 8,983,629 B2 | 3/2015 | Simon et al. |
| 8,996,116 B2 | 3/2015 | Faltys et al. |
| 9,114,262 B2 | 8/2015 | Libbus et al. |
| 9,162,064 B2 | 10/2015 | Faltys et al. |
| 9,174,041 B2 | 11/2015 | Faltys et al. |
| 9,211,409 B2 | 12/2015 | Tracey et al. |
| 9,211,410 B2 | 12/2015 | Levine et al. |
| 9,254,383 B2 | 2/2016 | Simon et al. |
| 9,272,143 B2 | 3/2016 | Libbus et al. |
| 9,358,381 B2 | 6/2016 | Simon et al. |
| 9,399,134 B2 | 7/2016 | Simon et al. |
| 9,403,001 B2 | 8/2016 | Simon et al. |
| 9,409,024 B2 | 8/2016 | KenKnight et al. |
| 9,415,224 B2 | 8/2016 | Libbus et al. |
| 9,452,290 B2 | 9/2016 | Libbus et al. |
| 9,504,832 B2 | 11/2016 | Libbus et al. |
| 9,511,228 B2 | 12/2016 | Amurthur et al. |
| 9,533,153 B2 | 1/2017 | Libbus et al. |
| 9,572,983 B2 | 2/2017 | Levine et al. |
| 9,662,490 B2 | 5/2017 | Tracey et al. |
| 9,700,716 B2 | 7/2017 | Faltys et al. |
| 9,833,621 B2 | 12/2017 | Levine |
| 9,849,286 B2 | 12/2017 | Levine et al. |
| 9,987,492 B2 | 6/2018 | Tracey et al. |
| 9,993,651 B2 | 6/2018 | Faltys et al. |
| 2001/0002441 A1 | 5/2001 | Boveja |
| 2001/0034542 A1 | 10/2001 | Mann |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0032852 A1 | 2/2003 | Perreault et al. |
| 2003/0045909 A1 | 3/2003 | Gross et al. |
| 2003/0088301 A1 | 5/2003 | King |
| 2003/0191404 A1 | 10/2003 | Klein |

(56) References Cited

U.S. PATENT DOCUMENTS

| | | |
|---|---|---|
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0002546 A1 | 1/2004 | Altschuler |
| 2004/0015202 A1 | 1/2004 | Chandler et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0049240 A1 | 3/2004 | Gerber et al. |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215272 A1 | 10/2004 | Haubrich et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0103351 A1 | 5/2005 | Stomberg et al. |
| 2005/0113894 A1 | 5/2005 | Zilberman et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0191661 A1 | 9/2005 | Gatanaga et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0277912 A1 | 12/2005 | John |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0136024 A1 | 6/2006 | Cohen et al. |
| 2006/0142802 A1 | 6/2006 | Armstrong |
| 2006/0142822 A1 | 6/2006 | Tulgar |
| 2006/0149337 A1 | 7/2006 | John |
| 2006/0155495 A1 | 7/2006 | Osorio et al. |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178703 A1 | 8/2006 | Huston et al. |
| 2006/0178706 A1 | 8/2006 | Lisogurski et al. |
| 2006/0190044 A1 | 8/2006 | Libbus et al. |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241697 A1 | 10/2006 | Libbus et al. |
| 2006/0241699 A1 | 10/2006 | Libbus et al. |
| 2006/0247719 A1 | 11/2006 | Maschino et al. |
| 2006/0247721 A1 | 11/2006 | Maschino et al. |

(56) References Cited

U.S. PATENT DOCUMENTS

| | | |
|---|---|---|
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129767 A1 | 6/2007 | Wahlstrand |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0198063 A1 | 8/2007 | Hunter et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0051852 A1 | 2/2008 | Dietrich et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0183226 A1 | 7/2008 | Buras et al. |
| 2008/0183246 A1 | 7/2008 | Patel et al. |
| 2008/0195171 A1 | 8/2008 | Sharma |
| 2008/0208266 A1 | 8/2008 | Lesser et al. |
| 2008/0213331 A1 | 9/2008 | Gelfand et al. |
| 2008/0234790 A1 | 9/2008 | Bayer et al. |
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0082832 A1 | 3/2009 | Carbunaru et al. |
| 2009/0088821 A1 | 4/2009 | Abrahamson |
| 2009/0105782 A1 | 4/2009 | Mickle et al. |
| 2009/0112291 A1 | 4/2009 | Wahlstrand et al. |
| 2009/0123521 A1 | 5/2009 | Weber et al. |
| 2009/0125079 A1 | 5/2009 | Armstrong et al. |
| 2009/0143831 A1 | 6/2009 | Huston et al. |
| 2009/0171405 A1 | 7/2009 | Craig |
| 2009/0177112 A1 | 7/2009 | Gharib et al. |
| 2009/0187231 A1 | 7/2009 | Errico et al. |
| 2009/0210042 A1 | 8/2009 | Kowalczewski |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0276019 A1 | 11/2009 | Perez et al. |
| 2009/0281593 A9 | 11/2009 | Errico et al. |
| 2009/0312817 A1 | 12/2009 | Hogle et al. |
| 2010/0003656 A1 | 1/2010 | Kilgard et al. |
| 2010/0010556 A1 | 1/2010 | Zhao et al. |
| 2010/0010571 A1 | 1/2010 | Skelton et al. |
| 2010/0010581 A1 | 1/2010 | Goetz et al. |
| 2010/0010603 A1 | 1/2010 | Ben-David et al. |
| 2010/0016746 A1 | 1/2010 | Hampton et al. |
| 2010/0042186 A1 | 2/2010 | Ben-David et al. |
| 2010/0063563 A1 | 3/2010 | Craig |
| 2010/0074934 A1 | 3/2010 | Hunter |
| 2010/0191304 A1 | 7/2010 | Scott |
| 2010/0215632 A1 | 8/2010 | Boss et al. |
| 2010/0241183 A1 | 9/2010 | DiLorenzo |
| 2010/0241207 A1 | 9/2010 | Bluger |
| 2010/0249859 A1 | 9/2010 | DiLorenzo |
| 2010/0280562 A1 | 11/2010 | Pi et al. |
| 2010/0280569 A1 | 11/2010 | Bobillier et al. |
| 2011/0004266 A1 | 1/2011 | Sharma |
| 2011/0054569 A1 | 3/2011 | Zitnik et al. |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0144717 A1 | 6/2011 | Burton et al. |
| 2011/0224749 A1 | 9/2011 | Ben-David et al. |
| 2011/0247620 A1 | 10/2011 | Armstrong et al. |
| 2011/0275927 A1 | 11/2011 | Wagner et al. |
| 2011/0307027 A1 | 12/2011 | Sharma et al. |
| 2012/0053657 A1 | 3/2012 | Parker et al. |
| 2012/0065706 A1 | 3/2012 | Vallapureddy et al. |
| 2012/0179219 A1 | 7/2012 | Kisker et al. |
| 2012/0185009 A1 | 7/2012 | Kornet et al. |
| 2012/0185020 A1 | 7/2012 | Simon et al. |
| 2013/0013016 A1 | 1/2013 | Diebold |
| 2013/0066392 A1 | 3/2013 | Simon et al. |
| 2013/0066395 A1 | 3/2013 | Simon et al. |
| 2013/0245718 A1 | 9/2013 | Birkholz et al. |
| 2013/0317580 A1 | 11/2013 | Simon et al. |
| 2014/0046407 A1 | 2/2014 | Ben-Ezra et al. |
| 2014/0206945 A1 | 7/2014 | Liao |
| 2014/0257425 A1 | 9/2014 | Arcot-Krishnamurthy et al. |
| 2014/0277260 A1 | 9/2014 | Khalil et al. |
| 2014/0288551 A1 | 9/2014 | Bharmi et al. |
| 2014/0330335 A1 | 11/2014 | Errico et al. |
| 2015/0018728 A1 | 1/2015 | Gross et al. |
| 2015/0100100 A1 | 4/2015 | Tracey et al. |
| 2015/0119956 A1 | 4/2015 | Libbus et al. |
| 2015/0180271 A1 | 6/2015 | Angara et al. |
| 2015/0233904 A1 | 8/2015 | Nayak |
| 2015/0241447 A1 | 8/2015 | Zitnik et al. |
| 2016/0067497 A1 | 3/2016 | Levine et al. |
| 2016/0114165 A1 | 4/2016 | Levine et al. |
| 2016/0250097 A9 | 9/2016 | Tracey et al. |
| 2016/0331952 A1 | 11/2016 | Faltys et al. |

(56) References Cited

U.S. PATENT DOCUMENTS

| | | | |
|---|---|---|---|
| 2016/0367808 | A9 | 12/2016 | Simon et al. |
| 2017/0113044 | A1 | 4/2017 | Levine et al. |
| 2017/0197076 | A1 | 7/2017 | Faltys et al. |
| 2017/0202467 | A1 | 7/2017 | Zitnik et al. |
| 2017/0203103 | A1 | 7/2017 | Levine et al. |
| 2017/0209705 | A1 | 7/2017 | Faltys et al. |
| 2017/0304613 | A1 | 10/2017 | Faltys et al. |
| 2018/0001096 | A1 | 1/2018 | Faltys et al. |
| 2018/0021217 | A1 | 1/2018 | Tracey et al. |
| 2018/0021580 | A1 | 1/2018 | Tracey et al. |
| 2018/0085578 | A1 | 3/2018 | Rennaker, II et al. |
| 2018/0117320 | A1 | 5/2018 | Levine et al. |
| 2018/0289970 | A1 | 10/2018 | Faltys et al. |
| 2019/0010535 | A1 | 1/2019 | Pujol Onofre et al. |
| 2019/0022389 | A1 | 1/2019 | Leonhardt |
| 2019/0192847 | A1 | 6/2019 | Faltys et al. |
| 2019/0290902 | A1 | 9/2019 | Romero-Ortega et al. |

FOREIGN PATENT DOCUMENTS

| | | |
|---|---|---|
| CN | 101578067 A | 11/2009 |
| CN | 101868280 A | 10/2010 |
| CN | 104220129 A | 12/2014 |
| DE | 2628045 A1 | 1/1977 |
| DE | 3736664 A1 | 5/1989 |
| DE | 20316509 U1 | 4/2004 |
| EP | 0438510 B1 | 8/1996 |
| EP | 0726791 B1 | 6/2000 |
| EP | 1001827 B1 | 1/2004 |
| EP | 2213330 A2 | 8/2010 |
| EP | 2073896 B1 | 10/2011 |
| GB | 04133 | 2/1910 |
| GB | 2073428 A | 10/1981 |
| KR | 20050039445 A | 4/2005 |
| WO | WO93/01862 A1 | 2/1993 |
| WO | WO97/30998 A1 | 8/1997 |
| WO | WO98/20868 A1 | 5/1998 |
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO03/072135 A2 | 9/2003 |
| WO | WO2004/000413 A2 | 12/2003 |
| WO | WO2004/064918 A1 | 8/2004 |
| WO | WO2006/073484 A1 | 7/2006 |
| WO | WO2006/076681 A2 | 7/2006 |
| WO | WO2007/133718 A2 | 11/2007 |
| WO | WO2010/005482 A1 | 1/2010 |
| WO | WO2010/067360 A2 | 6/2010 |
| WO | WO2010/118035 A2 | 10/2010 |
| WO | WO2016/134197 A1 | 8/2016 |

OTHER PUBLICATIONS

Koopman et al., Pilot study of stimulation of the cholinergic anti-inflammatory pathway with an implantable vagus nerve stimulation device in patients with rheumatoid arthritis; 2012 ACR/ARHP Annual Meeting; Abstract No. 451; 4 pages; retrieved from the internet (https://acrabstracts.org/abstract/pilot-study-of-stimulation-of-the-cholinergic-anti-inflammatory-pathway-with-an-implantable-vagus-nerve-stimulation-device-in-patients-with-rheumatoid-arthritis); (Abstract Only); on Sep. 24, 2020.
Pavlov et al.; The cholinergic anti-inflammatory pathway; Brain, Behavior, and Immunity; 19; p. 493-499; Nov. 2005.
Zitnik et al.; Treatment of chronic inflammatory diseases with implantable medical devices; Cleveland Clinic Journal of Medicine; 78(Suppl 1); pp. S30-S34; Aug. 2011.
Levine et al.; U.S. Appl. No. 16/916,036 entitled "Control of vagal simulation," filed Jun. 29, 2020.
Faltys et al.; U.S. Appl. No. 16/544,805 entitled "Nerve cuff with pocket for leadless stimulator," filed Aug. 19, 2019.
Faltys et al.; U.S. Appl. No. 16/544,882 entitled "Neural stimulation devices and systems for treatment of chronic inflammation," filed Aug. 19, 2019.
Levine et al.; U.S. Appl. No. 16/157,222 entitled "Vagus nerve stimulation to treat neurodegenerative disorders," filed Oct. 11, 2018.
Tracey et al., U.S. Appl. No. 16/231,581 entitled "Inhibition of inflammatory cytokine production by cholinergic agnostics and vagus nerve stimulation," filed Dec. 23, 2018.
Housley et al.; Biomarkers in multiple sclerosis; Clinical Immunology; 161(1); pp. 51-58; Nov. 2015.
Katsavos et al.; Biomarkers in multiple sclerosis: an up-to-date overview; Multiple Sclerosis International; vol. 2013, Article ID 340508, 20 pages; (year of pub. sufficiently earlier than effective US filing date and any foreign priority date) 2013.
Faltys et al.; U.S. Appl. No. 16/728,880 entitled "Implantable neurostimulator having power control and thermal regulation and methods of use," filed Dec. 27, 2019.
Faltys et al.; U.S. Appl. No. 16/785,400 entitled "Systems and methods for establishing a nerve block," filed Feb. 7, 2020.
Abraham, Coagulation abnormalities in acute lung injury and sepsis, Am. J. Respir. Cell Mol. Biol., vol. 22(4), pp. 401-404, Apr. 2000.
Aekerlund et al., Anti-inflammatory effects of a new tumour necrosis factor-alpha (TNF-Alpha) inhibitor (CNI-1493) in collagen-induced arthritis (CIA) in rats. Clinical & Experimental Immunology, vol. 115, No. 1, pp. 32-41, Jan. 1, 1999.
Anderson et al.; Reflex principles of immunological homeostasis; Annu. Rev. Immunol.; 30; pp. 313-335; Apr. 2012.
Antonica, A., et al., Vagal control of lymphocyte release from rat thymus, J. Auton. Nerv. Syst., vol. 48(3), pp. 187-197, Aug. 1994.
Asakura et al., Non-surgical therapy for ulcerative colitis, Nippon Geka Gakkai Zasshi, vol. 98, No. 4, pp. 431-437, Apr. 1997 (abstract only).
Beliavskaia et al.,"On the effects of prolonged stimulation of the peripheral segment of the vagus nerve . . . ," Fiziologicheskii Zhurnal SSSR Imeni I.M. Sechenova., vol. 52(11); p. 1315-1321, Nov. 1966.
Ben-Noun et al.; Neck circumference as a simple screening measure for identifying overweight and obese patients; Obesity Research; vol. 9; No. 8; pp. 470-477; Aug. 8, 2001.
Benoist, et al., "Mast cells in autoimmune disease" Nature., vol. 420(19): pp. 875-878, Dec. 2002.
Benthem et al.; Parasympathetic inhibition of sympathetic neural activity to the pancreas; Am.J.Physiol Endocrinol.Metab; 280(2); pp. E378-E381; Feb. 2001.
Bernik et al., Vagus nerve stimulation attenuates cardiac TNF production in endotoxic shock, (supplemental to SHOCK, vol. 15, 2001, Injury, inflammation and sepsis: laboratory and clinical approaches, SHOCK, Abstracts, 24th Annual Conference on Shock, Marco Island, FL, Jun. 9-12, 2001), Abstract No. 81.
Bernik et al., Vagus nerve stimulation attenuates endotoxic shock and cardiac TNF production, 87th Clinical Congress of the American College of Surgeons, New Orleans, LA, Oct. 9, 2001.
Bernik et al., Vagus nerve stimulation attenuates LPS-induced cardiac TNF production and myocardial depression IN shock, New York Surgical Society, New York, NY, Apr. 11, 2001.
Bernik, et al., Pharmacological stimulation of the cholinergic anti-inflammatory pathway, The Journal of Experimental Medicine, vol. 195, No. 6, pp. 781-788, Mar. 18, 2002.
Besedovsky, H., et al., Immunoregulatory feedback between interleukin-1 and glucocorticoid hormones, Science, vol. 233, No. 4764, pp. 652-654, Aug. 1986.
Bhattacharya, S.K. et al., Central muscarinic receptor subtypes and carrageenin-induced paw oedema in rats, Res. Esp. Med. vol. 191(1), pp. 65-76, Dec. 1991.
Bianchi et al., Suppression of proinflammatory cytokines in monocytes by a tetravalent guanylhydrazone, Journal of Experimental Medicine, vol. 183, pp. 927-936, Mar. 1996.

(56) References Cited

OTHER PUBLICATIONS

Biggio et al.; Chronic vagus nerve stimulation induces neuronal plasticity in the rat hippocampus; Int. J. Neurpsychopharmacol.; vol. 12; No. 9; pp. 1209-1221; Oct. 2009.
Blackwell, T. S. et al., Sepsis and cytokines; current status, Br. J. Anaesth., vol. 77(1), pp. 110-117, Jul. 1996.
Blum, A. et al., Role of cytokines in heart failure, Am. Heart J., vol. 135(2), pp. 181-186, Feb. 1998.
Boldyreff, Gastric and intestinal mucus, its properties and physiological importance, Acta Medica Scandinavica (journal), vol. 89, Issue 1-2, pp. 1-14, Jan./Dec. 1936.
Borovikova et al., Acetylcholine inhibition of immune response to bacterial endotoxin in human macrophages, Abstracts, Society for Neuroscience, 29th Annual Meeting, Miami Beach, FL, (Abs. No. 624.6); Oct. 23-28, 1999.
Borovikova et al., Efferent vagus nerve activity attenuates cytokine-mediated inflammation, Society for Neuroscience Abstracts, vol. 26, No. 102, Nov. 4-9, 2000 (abstract only).
Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.
Borovikova et al., Role of the efferent vagus nerve signaling in the regulation of the innate immune response to LPS, (supplemental to SHOCK, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.
Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).
Borovikova et al., Vagotomy blocks the protective effects of I.C.V. CNI-1493 against LPS-induced shock, (Supplemental to SHOCK, vol. 11, 1999, Molecular, cellular, and systemic pathobioloigal aspects and therapeutic approaches, abstacts and program, Fourth International Shock Congress and 22nd Annual Conference on Shock, Philadelphia, PA, Jun. 12-16, 1999), Abstract No. 277.
Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.
Borovikova, L. V., et al., Vagus nerve stimulation attenuates the systemic inflammatory response to endotoxin, Nature, vol. 405, No. 6785: pp. 458-462, May 25, 2000.
Bruchfeld et al.; Whole blood cytokine attenuation by cholinergic agonists ex vivo and relationship to vagus nerve activity in rheumatoid arthritis; J. Int. Med.; 268(1); pp. 94-101; Jul. 2010.
Bulloch et al.; Characterization of choline O-acetyltransferase (ChAT) in the BALB/C mouse spleen; Int.J.Neurosci.; 76(1-2); pp. 141-149; May 1994.
Bumgardner, G. L. et al., Transplantation and cytokines, Seminars in Liver Disease, vol. 19, No. 2, Thieme Medical Publishers; pp. 189-204, © 1999.
Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.
Bushby et al.; Centiles for adult head circumference; Archives of Disease in Childhood; vol. 67(10); pp. 1286-1287; Oct. 1992.
Cano et al.; Characterization of the central nervous system innervation of the rat spleen using viral transneuronal tracing; J.Comp Neurol.; 439(1); pp. 1-18; Oct. 2001.
Carteron, N. L., Cytokines in rheumatoid arthritis: trials and tribulations, Mol. Med. Today, vol. 6(8), pp. 315-323, Aug. 2000.
Cavaillon et al.; The pro-inflammatory cytokine casade; Immune Response in the Critically Ill; Springer-Verlag Berlin Hiedelberg; pp. 37-66; Jan. 21, 2002.
Cheyuo et al.; The parasympathetic nervous system in the quest for stroke therapeutics; J. Cereb. Blood Flow Metab.; 31(5); pp. 1187-1195; May 2011.
Cicala et al., "Linkage between inflammation and coagulation: An update on the molecular basis of the crosstalk," Life Sciences, vol. 62(20); pp. 1817-1824, Apr. 1998.
Clark et al.; Enhanced recognition memory following vagus nerve stimulation in human subjects; Nat. Neurosci.; 2(1); pp. 94-98; Jan. 1999.
Cohen, "The immunopathogenesis of sepsis," Nature., vol. 420(6917): pp. 885-891, Dec. 2002.
Corcoran, et al., The effects of vagus nerve stimulation on pro- and anti-inflammatory cytokines in humans: a preliminary report, NeuroImmunoModulation, vol. 12(5), pp. 307-309, Sep. 2005.
DAKE; Chronic cerebrospinal venous insufficiency and multiple sclerosis: Hostory and background; Techniques Vasc. Intervent. Radiol.; 15(2); pp. 94-100; Jun. 2012.
Das, Critical advances in spticemia and septic shock, Critical Care, vol. 4, pp. 290-296, Sep. 7, 2000.
Del Signore et al.; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.
Diamond et al.; Mapping the immunological homunculus; Proc. Natl. Acad. Sci. USA; 108(9); pp. 3461-3462; Mar. 1, 2011.
Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.
Dinarello, C. A., The interleukin-1 family: 10 years of discovery, Faseb J., vol. 8, No. 15, pp. 1314-1325, Dec. 1994.
Dorr et al.; Effect of vagus nerve stimulation on serotonergic and noradrenergic transmission; J. Pharmacol. Exp. Ther.; 318(2); pp. 890-898; Aug. 2006.
Doshi et al., Evolving role of tissue factor and its pathway inhibitor, Crit. Care Med., vol. 30, suppl. 5, pp. S241-S250, May 2002.
Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.
Ellington et al., In vitro selection of RNA molecules that bind specific ligands, Nature, vol. 346, pp. 818-822, Aug. 30, 1990.
Ellrich et al.; Transcutaneous vagus nerve stimulation; Eur. Neurological Rev.; 6(4); pp. 254-256; Winter 2011.
Engineer et al.; Directing neural plasticity to understand and treat tinnitus; Hear. Res.; 295; pp. 58-66; Jan. 2013.
Engineer et al.; Reversing pathological neural activity using targeted plasticity; Nature; 470(7332); pp. 101-104; Feb. 3, 2011 (Author Manuscript).
Esmon, The protein C pathway, Crit. Care Med., vol. 28, suppl. 9, pp. S44-S48, Sep. 2000.
Fields; New culprits in chronic pain; Scientific American; pp. 50-57; Nov. 2009.
Fleshner, M., et al., Thermogenic and corticosterone responses to intravenous cytokines (IL-1? and TNF-?) are attenuated by subdiaphragmatic vagotomy, J. Neuroimmunol., vol. 86(2), pp. 134-141, Jun. 1998.
Fox, D. A., Cytokine blockade as a new strategy to treat rheumatoid arthritis, Arch. Intern. Med., vol. 160, pp. 437-444, Feb. 28, 2000.
Fox, et al., Use of muscarinic agonists in the treatment of Sjorgren' syndrome, Clin. Immunol., vol. 101, No. 3; pp. 249-263, Dec. 2001.
Fujii et al.; Simvastatin regulates non-neuronal cholinergic activity in T lymphocytes via CD11a-mediated pathways; J. Neuroimmunol.; 179(1-2); pp. 101-107; Oct. 2006.
Gao et al.; Investigation of specificity of auricular acupuncture points in regulation of autonomic function in anesthetized rats; Autonomic Neurosc.; 138(1-2); pp. 50-56; Feb. 29, 2008.
Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.
Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.
Ghelardini et al., S-(-)-ET 126: A potent and selective M1 antagonist in vitro and in vivo, Life Sciences, vol. 58, No. 12, pp. 991-1000, Feb. 1996.

(56) References Cited

OTHER PUBLICATIONS

Ghia, et al., The vagus nerve: a tonic inhibitory influence associated with inflammatory bowel disease in a murine model, Gastroenterology, vol. 131, No. 4, pp. 1122-1130, Oct. 2006.
Giebelen, et al., Stimulation of ?7 cholinergic receptors inhibits lipopolysaccharide-induced neutrophil recruitment by a tumor necrosis factor ?-independent mechanism, SHOCK, vol. 27, No. 4, pp. 443-447, Apr. 2007.
Goyal et al., Nature of the vagal inhibitory innervation to the lower esophageal sphincter, Journal of Clinical Investigation, vol. 55, pp. 1119-1126, May 1975.
Gracie, J. A., et al., A proinflammatory role for IL-18 in rheumatoid arthritis, J. Clin. Invest., vol. 104, No. 10, pp. 1393-1401, Nov. 1999.
Granert et al., Suppression of macrophage activation with CNI-1493 increases survival in infant rats with systemic haemophilus influenzae infection, Infection and Immunity, vol. 68, No. 9, pp. 5329-5334, Sep. 2000.
Green et al., Feedback technique for deep relaxation, Psycophysiology, vol. 6, No. 3, pp. 371-377, Nov. 1969.
Gregory et al., Neutrophil-kupffer-cell interaction in host defenses to systemic infections, Immunology Today, vol. 19, No. 11, pp. 507-510, Nov. 1998.
Groves et al.; Recordings from the rat locus coeruleus during acute vagal nerve stimulation in the anaesthetised rat; Neuroscience Letters; 379(3); pp. 174-179; May 13, 2005.
Guarente, Leonard, Ph. D.; Sirtuins, Aging, and Medicine; N Engl J Med ; vol. 364:pp. 2235-2244; Jun. 2011.
Guslandi, M., Nicotine treatment for ulcerative colitis, Br. J. Clin. Pharmacol., vol. 48(4), pp. 481-484, Oct. 1999.
Hansson, E.; Could chronic pain and spread of pain sensation be induced and maintained by glial activation?. Acta Physiologica, vol. 187, Issue 1-2; p. 321R327, May/Jun. 2006.
Harrison's Principles of Internal Medicine, 13th Ed., pp. 511-515 and 1433-1435, Mar. 1994.
Hatton et al.; Vagal nerve stimulation: overview and implications for anesthesiologists; Int'l Anesthesia Research Society; vol. 103; No. 5; pp. 1241-1249; Nov. 2006.
Hirano, T., Cytokine suppresive agent improves survival rate in rats with acute pancreatitis of closed duodenal loop, J. Surg. Res., vol. 81, No. 2, pp. 224-229, Feb. 1999.
Hirao et al., The limits of specificity: an experimental analysis with RNA aptamers to MS2 coat protein variants, Mol. Divers., vol. 4, No. 2, pp. 75-89, 1999 (Accepted Jan. 13, 1999).
Hoffer et al.; Implantable electrical and mechanical interfaces with nerve and muscle; Annals of Biomedical Engineering; vol. 8; pp. 351-360; Jul. 1980.
Holladay et al., Neuronal nicotinic acetylcholine receptors as targets for drug discovery, Journal of Medicinal Chemistry, 40(26), pp. 4169-4194, Dec. 1997.
Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.
Hsu, et al., Analysis of efficiency of magnetic stimulation, IEEE Trans. Biomed. Eng., vol. 50(11), pp. 1276-1285, Nov. 2003.
Hsu, H. Y., et al., Cytokine release of peripheral blood monocluear cells in children with chronic hepatitis B virus infection, J. Pediatr. Gastroenterol., vol. 29, No. 5, pp. 540-545, Nov. 1999.
Hu, et al., The effect of norepinephrine on endotoxin-mediated macrophage activation, J. Neuroimmunol., vol. 31(1), pp. 35-42, Jan. 1991.
Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.
Huston et al.; Transcutaneous vagus nerve stimulation reduces serum high mobility group box 1 levels and improves survival in murine sepsis; Crit. Care Med.; 35(12); pp. 2762-2768; Dec. 2007.
Hutchinson et al.; Proinflammatory cytokines oppose opioid induced acute and chronic analgesia; Brain Behav Immun.; vol. 22; No. 8; pp. 1178-1189; Nov. 2008.
Ilton et al., "Differential expression of neutrophil adhesion molecules during coronary artery surgery with cardiopulmonary bypass" Journal of Thoracic and Cardiovascular Surgery, Mosby—Year Book, inc., St. Louis, Mo, US, pp. 930-937, Nov. 1, 1999.
Jaeger et al., The structure of HIV-1 reverse transcriptase complexed with an RNA pseudoknot inhibitor, The EMBO Journal, 17(15), pp. 4535-4542, Aug. 1998.
Jander, S. et al., Interleukin-18 is induced in acute inflammatory demyelinating polymeuropathy, J. Neuroimmunol., vol. 114, pp. 253-258, Mar. 2001.
Joshi et al., Potent inhibition of human immunodeficiency virus type 1 replection by template analog reverse transcriptase , J. Virol., 76(13), pp. 6545-6557, Jul. 2002.
Kawahara et al.; SIRT6 links histone H3 lysine 9 deacetylation to NF-kappaB-dependent gene expression and organismal life span.; Cell. ; vol. 136; No. 1; pp. 62-74; Jan. 2009.
Kalishevskaya et al. "The character of vagotomy-and atropin-induced hypercoagulation," Sechenov Physiological Journal of the USSR, 65(3): pp. 398-404, Mar. 1979.
Kalishevskaya et al.; Nervous regulation of the fluid state of the blood; Usp. Fiziol. Nauk;,vol. 13; No. 2; pp. 93-122; Apr.-Jun. 1982.
Kanai, T. et al., Interleukin-18 and Crohn's disease, Digestion, vol. 63, suppl. 1, pp. 37-42, (year of pub. sufficiently earlier than effective US filing date and any foreign priority date) 2001.
Katagiri, M., et al., Increased cytokine production by gastric mucosa in patients with helicobacter pylori infection, J. Clin, Gastroenterol., vol. 25, Suppl. 1, pp. S211-S214, 1997.
Kawashima, et al., Extraneuronal cholinergic system in lymphocytes, Pharmacology & Therapeutics, vol. 86, pp. 29-48, Apr. 2000.
Kees et al.; Via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.
Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.
Khatun, S., et al., "Induction of hypercoagulability condition by chronic localized cold stress in rabbits," Thromb. and Haemost., 81(3): pp. 449-455, Mar. 1999.
Kimball, et al., Levamisole causes differential cytokine expression by elicited mouse peritoneal macrophases, Journal of Leukocyte Biology, vo. 52, No. 3, pp. 349-356, Sep 1992 (abstract only).
Kimmings, A. N., et al., Systemic inflammatory response in acute cholangitis and after subsequent treatment, Eur. J. Surg., vol. 166, pp. 700-705, Sep. 2000.
Kirchner et al.; Left vagus nerve stimulation suppresses experimentally induced pain; Neurology; vol. 55; pp. 1167-1171; Oct. 2000.
Kokkula, R et al., Successful treatment of collagen-induced arthritis in mice and rats by targeting extracellular high mobility group box chromosomal protein 1 activity, Arthritis Rheum., 48(7), pp. 2052-2058, Jul. 2003.
Koopman et al.; Pilot study of stimulation of the cholinergic anti-inflammatory pathway with an implantable vagus nerve stimulation device in patients with rheumatoid arthritis; Arth. Rheum.; 64(10 suppl.); pp. S195; Oct. 2012.
Krarup et al.; Conduction studies in peripheral cat nerve using implanted electrodes: I. methods and findings in controls; Muscle & Nerve; vol. 11; pp. 922-932; Sep. 1988.
Kudrjashov, et al. "Reflex nature of the physiological anticoagulating system," Nature, vol. 196(4855): pp. 647-649; Nov. 17, 1962.
Kumins, N. H., et al., Partial hepatectomy reduces the endotoxin-induced peak circulating level of tumor necrosis factor in rats, SHOCK, vol. 5, No. 5, pp. 385-388, May 1996.
Kuznik, "Role of the vascular wall in the process of hemostatis," Usp Sovrem Biol., vol. 75(1): pp. 61-85, (year of pub. sufficiently earlier than effective US filing date and any foreign priority date)1973.

(56) References Cited

OTHER PUBLICATIONS

Kuznik, et al., "Blood Coagulation in stimulation of the vagus nerve in cats," Biull. Eskp. Biol. Med., vol. 78(7): pp. 7-9, (year of pub. sufficiently earlier than effective US filing date and any foreign priority date) 1974.
Kuznik, et al., "Heart as an efferent regulator of the process of blood coagulation and fibrinolysis," Kardiologiia, vol. 13(3): pp. 10-17, (year of pub. sufficiently earlier than effective US filing date and any foreign priority date) 1973.
Kuznik, et al., "Role of the heart and vessels in regulating blood coagulation and fibrinolysis," Kagdiologiia, vol. 13(4): pp. 145-154, Apr. 1973.
Kuznik, et al., "Secretion of blood coagulation factors into saliva under conditions of hypo-and hypercoagulation," Voprosy Meditsinskoi Khimii, vol. 19(1): pp. 54-57; (year of pub. sufficiently earlier than effective US filing date and any foreign priority date) 1973.
Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.
Kuznik, et al., "The role of the vascular wall in the mechanism of control of blood coagulation and fibrinolysis on stimulation of the vagus nerve," Cor Vasa, vol. 17(2): pp. 151-158, (year of pub. sufficiently earlier than effective US filing date and any foreign priority date) 1975.
Lang, et al., "Neurogienic control of cerebral blood flow," Experimental Neurology, 43(1): pp. 143-161, Apr. 1974.
Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.
LeNovere, N. et al., Molecular evolution of the nicotinic acetylcholine receptor: an example of multigene family in excitable cells, J. Mol. Evol., 40, pp. 155-172, Feb. 1995.
Leonard, S. et al., Neuronal nicotinic receptors: from structure to function, Nicotine & Tobacco Res. 3:203-223, Aug. 2001.
Lips et al.; Coexpression and spatial association of nicotinic acetylcholine receptor subunits alpha7 and alpha10 in rat sympathetic neurons; J.Mol.Neurosci.; 30; pp. 15-16; Feb. 2006.
Lipton, J. M. et al.; Anti-inflammatory actions of the neuroimmunomodulator ?-MSH, Immunol. Today, vol. 18, pp. 140-145, Mar. 1997.
Loeb et al.; Cuff electrodes for chronic stimulation and recording of peripheral nerve activity; Journal of Neuroscience Methods; vol. 64; pp. 95-103; Jan. 1996.
Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.
Manta et al.; Optimization of vagus nerve stimulation parameters using the firing activity of serotonin neurons in the rat dorsal raphe; European Neuropsychopharmacology; vol. 19; pp. 250-255; Jan. 2009 (doi: 10.1016/j.euroneuro.2008.12.001).
Martindale: The Extra Pharmacopoeia; 28th Ed. London; The Pharmaceutical Press; pp. 446-485; © 1982.
Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.
McGuinness, P. H., et al., Increases in intrahepatic CD68 positive cells, MAC387 positive cells, and proinflammatory cytokines (particulary interleukin 18) in chronic hepatitis C infection, Gut, vol. 46(2), pp. 260-269, Feb. 2000.
Miguel-Hidalgo, J. J.; The role of glial cells in drug abuse; Current Drug Abuse Reviews; vol. 2; No. 1; pp. 76-82; Jan. 2009.
Milligan et al.; Pathological and protective roles of glia in chronic pain; Nat Rev Neurosci.; vol. 10; No. 1; pp. 23-26; Jan. 2009.
Minnich et al.; Anti-cytokine and anti-inflammatory therapies for the treatment of severe sepsis: progress and pitfalls; Proceedings of the Nutrition Society; vol. 63(3); pp. 437-441; Aug. 2004.

Mishchenko, et al., "Coagulation of the blood and fibrinolysos in dogs during vagal stimulation," Sechenov Physiological Journal of the USSR, vol. 61(1): pp. 101-107, 1975.
Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, 1974.
Molina et al., CNI-1493 attenuates hemodynamic and proinflammatory responses to LPS, Shock, vol. 10, No. 5, pp. 329-334, Nov. 1998.
Nadol et al., "Surgery of the Ear and Temporal Bone," Lippinkott Williams & Wilkins, 2nd Ed., 2005, (Publication date: Sep. 21, 2004), p. 580.
Nagashima et al., Thrombin-activatable fibrinolysis inhibitor (TAFI) deficiency is compatible with murine life, J. Clin. Invest., 109, pp. 101-110, Jan. 2002.
Nathan, C. F., Secretory products of macrophages, J. Clin. Invest., vol. 79(2), pp. 319-326, Feb. 1987.
Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.
Navzer et al.; Reversing pathological neural activity using targeted plasticity; Nature; 470(7332); pp. 101-104; Feb. 3, 2011.
Neuhaus et al.; P300 is enhanced in responders to vagus nerve stimulation for treatment of major depressive disorder; J. Affect. Disord.; 100(1-3); pp. 123-128; Jun. 2007.
Noguchi et al., Increases in Gastric acidity in response to electroacupuncture stimulation of hindlimb of anesthetized rats, Jpn. J. Physiol., 46(1), pp. 53-58, Feb. 1996.
Norton, Can ultrasound be used to stimulate nerve tissue, BioMedical Engineering OnLine, 2(1), pp. 6, Mar. 4, 2003.
Olofsson et al.; Rethinking inflammation: neural circuits in the regulation of immunity; Immunological Reviews; 248(1); pp. 188-204; Jul. 2012.
Oshinsky et al.; Non-invasive vagus nerve stimulation as treatment for trigeminal allodynia; Pain; 155(5); pp. 1037-1042; May 2014.
Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.
Pateyuk, et al.,"Treatment of Botkin's disease with heparin," Klin. Med., vol. 51(3): pp. 113-117, Mar. 1973.
Pavlov et al; Controlling inflammation: the cholinergic antiinflammatory pathway; Biochem. Soc. Trans.; 34(Pt 6); pp. 1037-1040; Dec. 2006.
Payne, J. B. et al., Nicotine effects on PGE2 and IL-1 beta release by LPS-treated human monocytes, J. Perio. Res., vol. 31, No. 2, pp. 99-104, Feb. 1996.
PEUKER; The nerve supply of the human auricle; Clin. Anat.; 15(1); pp. 35-37; Jan. 2002.
Pongratz et al.; The sympathetic nervous response in inflammation; Arthritis Research and Therapy; 16(504); 12 pages; retrieved from the internet (http://arthritis-research.com/content/16/6/504); Jan. 2014.
Prystowsky, J. B. et al., Interleukin-1 mediates guinea pig gallbladder inflammation in vivo, J. Surg. Res., vol. 71, No. 2, pp. 123-126, Aug. 1997.
Pulkki, K. J., Cytokines and cardiomyocyte death, Ann. Med., vol. 29(4), pp. 339-343, Aug. 1997.
Pullan, R. D., et al., Transdermal nicotine for active ulceratiive colitis, N. Engl. J. Med., vol. 330, No. 12, pp. 811-5, Mar. 24, 1994.
Pulvirenti et al.; Drug dependence as a disorder of neural plasticity:focus on dopamine and glutamate; Rev Neurosci.; vol. 12; No. 2; pp. 141-158; Apr./Jun. 2001.
Rahman et al.; Mammalian Sirt 1: Insights on its biological functions; Cell Communications and Signaling; vol. 9; No. 11; pp. 1-8; May 2011.
Rayner, S. A. et al., Local bioactive tumour necrosis factor (TNF) in corneal allotransplantation, Clin. Exp. Immunol., vol. 122, pp. 109-116, Oct. 2000.
Reale et al.; Treatment with an acetylcholinesterase inhibitor in alzheimer patients modulates the expression and production of the

(56) References Cited

OTHER PUBLICATIONS pro-inflammatory and anti-inflammatory cytokines; J. Neuroimmunology; 148(1-2); pp. 162-171; Mar. 2004.
Rinner et al.; Rat lymphocytes produce and secrete acetylcholine in dependence of differentiation and activation; J.Neuroimmunol.; 81(1-2); pp. 31-37; Jan. 1998.
Robinson et al.; Studies with the Electrocardiograph on the Action of the Vagus Nerve on the Human Heart; J Exp Med; 14(3):217-234; Sep. 1911.
Romanovsky, A. A., et al.,The vagus nerve in the thermoregulatory response to systemic inflammation, Am. J. Physiol., vol. 273, No. 1 (part 2), pp. R407-R413, Jul. 1, 1997.
Saghizadeh et al.; The expression of TNF? by human muscle; J. Clin. Invest.; vol. 97; No. 4; pp. 1111-1116; Feb. 15, 1996.
Saindon et al.; Effect of cervical vagotomy on sympathetic nerve responses to peripheral interleukin-1beta; Auton.Neuroscience Basic and Clinical; 87; pp. 243-248; Mar. 23, 2001.
Saito, Involvement of muscarinic M1 receptor in the central pathway of the serotonin-induced bezold-jarisch reflex in rats, J. Autonomic Nervous System, vol. 49, pp. 61-68, Sep. 1994.
Sandborn, W. J., et al., Transdermal nicotine for mildly to moderately active ulcerative colitis, Ann. Intern. Med, vol. 126, No. 5, pp. 364-371, Mar. 1, 1997.
Sato, E., et al., Acetylcholine stimulates alveolar macrophages to release inflammatory cell chemotactic activity, Am. J. Physiol., vol. 274, pp. L970-L979, Jun. 1998.
Sato, K.Z., et al., Diversity of mRNA expression for muscarinic acetylcholine receptor subtypes and neuronal nicotinic acetylcholine receptor subunits in human mononuclear leukosytes and leukemic cell lines, Neuroscience Letters, vol. 266, pp. 17-20, Apr. 30, 1999.
Scheinman, R. I., et al., Role of transcriptional activation of I?B? in mediation of immunosuppression by glucocorticoids, Science, vol. 270, No. 5234, pp. 283-286, Oct. 13, 1995.
Schneider et al., High-affinity ssDNA inhibitors of the review transcriptase of type 1 human immunodeficiency virus, Biochemistry, 34(29), pp. 9599-9610, Jul. 1995.
Shafer, Genotypic testing for human immunodeficiency virus type 1 drug resistance, Clinical Microbiology Reviews, vol. 15, pp. 247-277, Apr. 2002.
Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.
Sher, M. E., et al., The influence of cigarette smoking on cytokine levels in patients with inflammatory bowel disease, Inflamm. Bowel Dis., vol. 5, No. 2, pp. 73-78, May 1999.
Shi et al.; Effects of efferent vagus nerve excitation on inflammatory response in heart tissue in rats with endotoxemia; vol. 15, No. 1; pp. 26-28; Jan. 2003 (Eng. Abstract).
Snyder et al., Correction of hemophilia B in canine and murine models using recombinant adeno-associated viral vectors; Nature Medicine, 5(1), pp. 64-70, Jan. 1999.
Sokratov, et al. "The role of choline and adrenegic structures in regulation of renal excretion of hemocoagulating compounds into the urine," Sechenov Physiological Journal of the USSR, vol. 63(12): pp. 1728-1732, 1977.
Stalcup et al., Endothelial cell functions in the hemodynamic responses to stress, Annals of the New York Academy of Sciences, vol. 401, pp. 117-131, Dec. 1982.
Steinlein, New functions for nicotine acetylcholine receptors?, Behavioural Brain Res., vol. 95(1), pp. 31-35, Sep. 1998.
Sternberg, E. M., Perspectives series: cytokines and the brain 'neural-immune interactions in health and disease,' J. Ciin. Invest., vol. 100, No. 22, pp. 2641-2647, Dec. 1997.
Stevens et al.; The anti-inflammatory effect of some immunosuppressive agents; J. Path.; 97(2); pp. 367-373; Feb. 1969.
Strojnik et al.; Treatment of drop foot using and implantable peroneal underknee stimulator; Scand. J. Rehab. Med.; vol. 19(1); p. 37R43; Dec. 1986.
Sugano et al., Nicotine inhibits the production of inflammatory mediators in U937 cells through modulation of nuclear factor-kappaβ activation, Biochemical and Biophysical Research Communications, vol. 252, No. 1, pp. 25-28, Nov. 9, 1998.
Suter et al.; Do glial cells control pain?; Neuron Glia Biol.; vol. 3; No. 3; pp. 255-268; Aug. 2007.
Swick et al.; Locus coeruleus neuronal activity in awake monkeys: relationship to auditory P300-like potentials and spontaneous EEG. Exp. Brain Res.; 101(1); pp. 86-92; Sep. 1994.
Sykes, et al., An investigation into the effect and mechanisms of action of nicotine in inflammatory bowel disease, Inflamm. Res., vol. 49, pp. 311-319, Jul. 2000.
Takeuchi et al., A comparision between Chinese blended medicine "Shoseiryuto" tranilast and ketotifen on the anit-allergic action in the guinea pigs, Allergy, vol. 34, No. 6, pp. 387-393, Jun. 1985 (eng. abstract).
Tekdemir et al.; A clinico-anatomic study of the auricular branch of the vagus nerve and arnold's ear-cough reflex; Surg. Radiol. Anat.; 20(4); pp. 253-257; Mar. 1998.
Toyabe, et al., Identification of nicotinic acetylcholine receptors on lymphocytes in the periphery as well as thymus in mice, Immunology, vol. 92(2), pp. 201-205, Oct. 1997.
Tracey et al., Mind over immunity, Faseb Journal, vol. 15, No. 9, pp. 1575-1576, Jul. 2001.
Tracey, K. J. et al., Anti-cachectin/TNF monoclonal antibodies prevent septic shock during lethal bacteraemia; Nature, 330: pp. 662-664, Dec. 23, 1987.
Tracey, K. J. et al., Physiology and immunology of the cholinergic antiinflammatory pathway; J Clin Invest.; vol. 117: No. 2; pp. 289-296; Feb. 2007.
Tracey, K. J.; Reflex control of immunity; Nat Rev Immunol; 9(6); pp. 418-428; Jun. 2009.
Tracey, K. J. et al., Shock and tissue injury induced by recombinant human cachectin, Science, vol. 234, pp. 470-474, Oct. 24, 1986.
Tracey, K.J., The inflammatory reflex, Nature, vol. 420, pp. 853-859, Dec. 19-26, 2002.
Tsutsui, H., et al., Pathophysiolocical roles of interleukin-18 in inflammatory liver diseases; Immunol. Rev., 174:192-209, Apr. 2000.
Tuerk et al., RNA pseudoknots that inhibit human immunodeficiency virus type 1 reverse transcriptase; Proc. Natl. Acad. Sci. USA, 89, pp. 6988-6992, Aug. 1992.
Tuerk et al., Systematic evolution of ligands by exponential enrichment: RNA ligands to bacteriophage T4 DNA polymerase; Science, 249(4968), pp. 505-510, Aug. 3, 1990.
Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.
Van Der Horst et al.; Stressing the role of FoxO proteins in lifespan and disease; Nat Rev Mol Cell Biol.; vol. 8; No. 6; pp. 440-50; Jun. 2007.
Vanhoutte, et al., Muscarinic and beta-adrenergic prejunctional modulation of adrenergic neurotransmission in the blood vessel wall, Gen Pharmac., vol. 14(1), pp. 35-37, Jan. 1983.
VanWesterloo, et al., The cholinergic anti-inflammatory pathway regulates the host response . during septic peritonitis, The Journal of Infectious Diseases, vol. 191, pp. 2138-2148, Jun. 15, 2005.
Ventureyra, Transcutaneous vagus nerve stimulation for partial onset seizure therapy, Child's Nerv Syst, vol. 16(2), pp. 101-102, Feb. 2000.
Vijayaraghavan, S.; Glial-neuronal interactions-implications for plasticity anddrug addictionl AAPS J.; vol. 11; No. 1; pp. 123-132; Mar. 2009.
Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.
Von Känel, et al., Effects of non-specific ?-adrenergic stimulation and blockade on blood coagulation in hypertension, J. Appl. Physiol., vol. 94, pp. 1455-1459, Apr. 2003.
Von Känel, et al., Effects of sympathetic activation by adrenergic infusions on hemostasis in vivo, Eur. J. Haematol., vol. 65: pp. 357-369, Dec. 2000.

(56) References Cited

OTHER PUBLICATIONS

Walland et al., Compensation of muscarinic brochial effects of talsaclidine by concomitant sympathetic activation in guinea pigs; European Journal of Pharmacology, vol. 330(2-3), pp. 213-219, Jul. 9, 1997.

Wang et al; Nicotinic acetylcholine receptor alpha7 subunit is an essential regulator of inflammation; Nature; 421; 384-388; Jan. 23, 2003.

Wang, H., et al., HMG-1 as a late mediator of endotoxin lethality in mice, Science, vol. 285, pp. 248-251, Jul. 9, 1999.

Waserman, S. et al., TNF-? dysregulation in asthma: relationship to ongoing corticosteroid therapy, Can. Respir. J., vol. 7, No. 3, pp. 229-237, May-Jun. 2000.

Watanabe, H et al., The significance of tumor necrosis factor (TNF) levels for rejection of joint allograft, J. Reconstr. Microsurg., vol. 13, No. 3, pp. 193-197, Apr. 1997.

Wathey, J.C. et al., Numerical reconstruction of the quantal event at nicotinic synapses; Biophys. J., vol. 27: pp. 145-164, Jul. 1979.

Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.

Watkins, L.R. et al., Implications of immune-to-brain communication for sickness and pain, Proc. Natl. Acad. Sci. U.S.A., vol. 96(14), pp. 7710-7713, Jul. 6, 1999.

Webster's Dictionary, definition of "intrathecal", online version accessed Apr. 21, 2009.

Weiner, et al., "Inflammation and therapeutic vaccination in CNS diseases," Nature., vol. 420(6917): pp. 879-884, Dec. 19-26, 2002.

Westerheide et al.; Stress-inducible regulation of heat shock factor 1 by the deacetylase SIRT1.; Science; Vo. 323; No. 5717; pp. 1063-6; Feb. 2009.

Whaley, K. et al., C2 synthesis by human monocytes is modulated by a nicotinic cholinergic receptor, Nature, vol. 293, pp. 580-582, Oct. 15, 1981.

Woiciechowsky, C. et al., Sympathetic activation triggers systemic interleukin-10 release in immunodepression induced by brain injury, Nature Med., vol. 4, No. 7, pp. 808-813, Jul. 1998.

Yeh, S.S. et al., Geriatric cachexia; the role of cytokines, Am. J. Clin. Nutr., vol. 70(2), pp. 183-197, Aug. 1999.

Yu et al.; Low-level transcutaneous electrical stimulation of the auricular branch of the vagus nerve: a non-invasive approach to treat the initial phase of atrial fibrillation; Heart Rhythm; 10(3); pp. 428-435; Mar. 2013.

Zamotrinsky et al.; Vagal neurostimulation in patients with coronary artery disease; Auton. Neurosci.; 88(1-2); pp. 109-116; Apr. 2001.

Zhang et al., Tumor necrosis factor, The Cytokine Handbook, 3rd ed., Ed. Thompson, Academic Press, pp. 517-548, Jul. 1, 1998.

Zhang et al.; Roles of SIRT1 in the acute and restorative phases following induction of inflammation.; J Biol Chem.; vol. 285; No. 53; pp. 41391-401; Dec. 2010.

Zhang et al.; Chronic vagus nerve stimulation improves autonomic control and attenuates systemic inflammation and heart failure progression in a canine high-rate pacing model; Circulation Heart Fail.; 2; pp. 692-699; Nov. 2009.

Zhao et al.; Transcutaneous auricular vagus stimulation protects endotoxemic rat from lipopolysaccharide-induced inflammation; Evid. Based Complement Alternat. Med.; vol. 2012; Article ID 627023; 10 pages; Dec. 29, 2012.

Zitnik et al.; U.S. Appl. No. 16/356,906 entitled "Batteryless Implantable Microstimulators," filed Mar. 18, 2019.

Crusz et al.; Inflammation and cancer; advances and new agents; Nature reviews Clinical Oncology; 12(10); pp. 584-596; doi: 10.1038/nrclinonc.2015.105; Jun. 30, 2015.

Strowig et al.; Inflammasomes in health and disease; Nature; vol. 481; pp. 278-286; doi: 10.1038/nature10759; Jan. 19, 2012.

Manogue; U.S. Appl. No. 16/582,726 entitled "Methods and apparatuses for reducing bleeding via coordinated trigeminal and vagal nerve stimulation," filed Sep. 25, 2019.

Palov et al.; The cholinergic anti-inflammatory pathway: a missing link in neuroimmunomodulation; Molecular Medicine; 9(5); pp. 125-134; May 2003.

Tracey et al.; U.S. Appl. No. 17/170,772 entitled "Treatment of bleeding by non-invasive stimulation," filed Feb. 8, 2021.

FIG. 4A
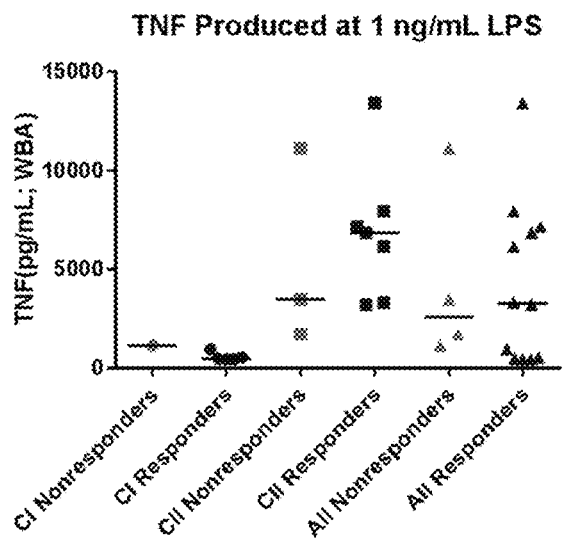
FIG. 4B
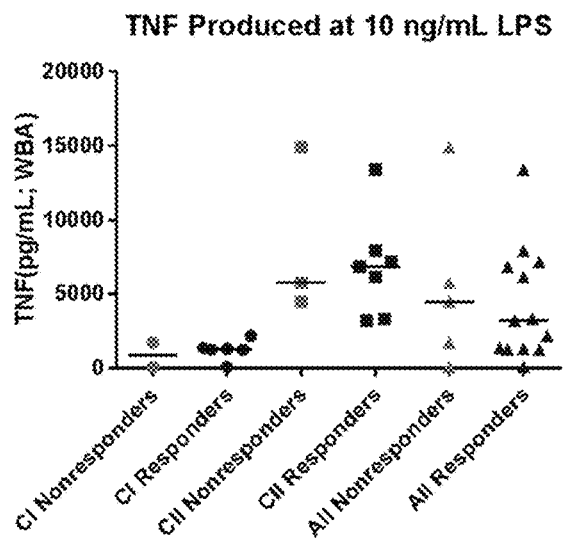
FIG. 4C

|  |  | 1) Increase and 2) Decrease and CD14+CD11b+CD15+ | Decrease Decrease and CD3-CD19+ | Increase CD14+CD16-CCR2+CX3CR1- |
|---|---|---|---|---|
| Non-Responders | 0901-005 | 106 | 88 † | 128 * |
|  | 0901-006 | 79 † | 83 † | 274 * |
|  | 0901-012 | 126 * | 71 † | 90 † |
|  | 0901-001 | 119 * | 84 † | 52 † |
|  | 2401-002 | 81 † | 64 † | 155 * |
| Responders | 0901-002 | 108 | 93 | 183 * |
|  | 0901-004 | 101 | 97 | 79 † |
|  | 0901-007 | 46 † | 96 | 50 † |
|  | 0901-009 | 98 | 72 † | 111 * |
|  | 0901-010 | 89 † | 42 † | 62 † |
|  | 0901-011 |  | 72 † |  |
|  | 0901-013 | 105 | 108 | 48 † |
|  | 0901-014 | 24 † | 182 * | 20 † |
|  | 2402-001 | 83 † | 55 † | 96 |
|  | 0901-003 | 60 † | 189 * | 24 † |
|  | 2306-001 | 58 † | 110 * | 229 * |
|  | 2306-002 |  |  |  |
|  | 2402-006 | 126 * | 142 * | 862 * |

CD14+CD11b+CD15+ Monocyte Subset
CD3-CD19+ B-lymphocytes
CD14+CD16-CCR2+CX3CR1- Monocyte Subset Increase *
Decrease †
Δ≤10%

FIG. 12

|  |  | 1) Decrease and CD3-CD19+ | Decrease IL-7 |
|---|---|---|---|
| Non-Responders | 0901-005 | 88 ↓ | 80 ↓ |
|  | 0901-006 | 83 ↓ | 68 ↓ |
|  | 0901-012 | 71 ↓ | 82 ↓ |
|  | 0901-001 | 84 ↓ | 76 ↓ |
|  | 2401-002 | 64 ↓ | 82 ↓ |
| Responders | 0901-002 | 93 | 101 |
|  | 0901-004 | 97 | 132 * |
|  | 0901-007 | 96 | 84 ↓ |
|  | 0901-009 | 72 ↓ | 91 |
|  | 0901-010 | 42 ↓ | 133 * |
|  | 0901-011 | 72 ↓ | 100 |
|  | 0901-013 | 108 | 96 |
|  | 0901-014 | 182 * | 106 |
|  | 2402-001 | 55 ↓ | 155 * |
|  | 0901-003 | 189 * | 86 ↓ |
|  | 2306-001 | 110 * | 144 * |
|  | 2306-002 |  | 52 ↓ |
|  | 2402-006 | 142 * | 96 |

Increase *
Decrease ↓
Δ≤10%

CD3-CD19+ B-lymphocytes

IL-7 is involved in B cell and T cell maturation

FIG. 13

VAGUS NERVE STIMULATION PRE-SCREENING TEST

CROSS REFERENCE TO RELATED APPLICATIONS

This patent application claims priority to U.S. Provisional Patent Application No. 62/545,284, filed on Aug. 14, 2017, and titled "VAGUS NERVE STIMULATION PRE-SCREENING TEST," which is herein incorporated by reference in its entirety.

The pre-screening methods and apparatuses described herein may be related to therapies and apparatuses such as those described in one or more of: the following U.S. patent applications: U.S. patent application Ser. No. 14/630,613, filed on Feb. 24, 2015, titled "VAGUS NERVE STIMULATION SCREENING TEST," now U.S. Patent Publication No. 2015/0241447; U.S. patent application Ser. No. 12/620, 413, filed on Nov. 17, 2009, titled "DEVICES AND METHODS FOR OPTIMIZING ELECTRODE PLACEMENT FOR ANTI-INFLAMATORY STIMULATION," now U.S. Pat. No. 8,412,338; U.S. patent application Ser. No. 12/874, 171, filed on Sep. 1, 2010, titled "PRESCRIPTION PAD FOR TREATMENT OF INFLAMMATORY DISORDERS," Publication No. US-2011-0054569-A1; U.S. patent application Ser. No. 12/917,197, filed on Nov. 1, 2010, titled "MODULATION OF THE CHOLINERGIC ANTI-INFLAMMATORY PATHWAY TO TREAT PAIN OR ADDICTION," Publication No. US-2011-0106208-A1; U.S. patent application Ser. No. 12/978,250, filed on Dec. 23, 2010, titled "NEURAL STIMULATION DEVICES AND SYSTEMS FOR TREATMENT OF CHRONIC INFLAMMATION," now U.S. Pat. No. 8,612,002; U.S. patent application Ser. No. 12/797,452, filed on Jun. 9, 2010, titled "NERVE CUFF WITH POCKET FOR LEADLESS STIMULATOR," now U.S. Pat. No. 8,886,339; U.S. patent application Ser. No. 13/467,928, filed on May 9, 2012, titled "SINGLE-PULSE ACTIVATION OF THE CHOLINERGIC ANTI-INFLAMMATORY PATHWAY TO TREAT CHRONIC INFLAMMATION," now U.S. Pat. No. 8,788, 034; and U.S. patent application Ser. No. 13/338,185, filed on Dec. 27, 2011, titled "MODULATION OF SIRTUINS BY VAGUS NERVE STIMULATION," Publication No. US-2013-0079834-A1. Each of these patent applications is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference. The following is a list of publications that are incorporated by reference:

Andersson U, Tracey K. Reflex principles of immunological homeostasis. Annu Rev Immunol 2012; 30:313.
Bruchfeld A, et al. Whole blood cytokine attenuation by cholinergic agonists ex vivo and relationship to vagus nerve activity in rheumatoid arthritis. J Int Med 2010; 268:94.
Dake M. Chronic cerebrospinal venous insufficiency and multiple sclerosis: Hostory and background. Techniques Vasc Intervent Radiol 2012; 15:94.
Ellrich J. Transcutaneous vagus nerve stimulation. Eur Neurological Rev 2011; 6:254-256.
Gao X, et al. Investigation of specificity of auricular acupuncture points in regulation of autonomic function in anesthetized rats. Autonomic Neurosc 1998; 88:109.
Huston J, et al. Transcutaneous vagus nerve stimulation reduces serum high mobility group box 1 levels and improves survival in murine sepsis. Crit Care Med 2007; 12:2762.
Koopman F, et al. Pilot study of stimulation of the cholinergic anti-inflammatory pathway with an implantable vagus nerve stimulation device in patients with rheumatoid arthritis. Arth Rheum 2012; 64 (10 suppl):S195.
M. L. Oshinsky, A. L. Murphy, H. Hekierski Jr., M. Cooper, B. J. Simon, Non-Invasive Vagus Nerve Stimulation as Treatment for Trigeminal Allodynia, PAIN (2014), doi: http://dx.doi.org/10.1016/j.pain.2014.02.009.
Peuker E. The nerve supply of the human auricle. Clin Anat 2002; 15:35.
Tekdemir I, et al. A clinico-anatomic study of the auricular branch of the vagus nerve and Arnold's ear-cough reflex. Surg Radiol Anat 1998; 20:253.
Yu L, et al. Low-level transcutaneous electrical stimulation of the auricular branch of the vagus nerve: A non-invasive approach to treat the initial phase of atrial fibrillation. Heart Rhythm 2013; 10: 428.
Zhao Y, et al. Transcutaneous auricular vagus nerve stimulation protects endotoxemic rat from lipopolysaccharide-induced inflammation. Evid Based Complement Alternat Med. 2012; 2012:627023. doi: 10.1155/2012/627023. Epub 2012 Dec. 29.

FIELD

Embodiments of the invention relate generally to systems and methods for using vagus nerve stimulation for treatment, and more specifically to pre-screening methods and apparatuses for identifying patient that may respond to vagus nerve stimulation treatment for the treatment of inflammatory disorders.

BACKGROUND

The vagus nerve mediates the inflammatory reflex, a mechanism the central nervous system utilizes to regulate innate and adaptive immunity. The afferent arm of the reflex senses inflammation both peripherally and in the central nervous system, and down-regulates the inflammation via efferent neural outflow. The efferent arm of this reflex has been termed the "cholinergic anti-inflammatory pathway" (CAP). The reflex serves as a physiological regulator of inflammation by responding to environmental injury and pathogens with an appropriate degree of immune system activation (Andersson, 2012). CAP activation can also be harnessed to reduce pathological inflammation. Activating the CAP chronically using electrical neurostimulation of the vagus nerve is a feasible means of treating diseases characterized by excessive and dysregulated inflammation.

Although vagus nerve stimulation has been shown to be effective in some patients, the efficacy of the treatment may vary, particularly at low to moderate stimulation levels. Responders are those patient's that response strongly to vagus nerve stimulation, particularly for the treatment of inflammatory disorders, including those described above, and incorporated by reference. However, there are some patients for whom vagus nerve stimulation alone, and particularly electrical vagus nerve stimulation, may not be sufficient. These patients may be referred to as non-responders or low responders. It would be particularly helpful to be able to a priori determine if a particular patient will respond well to a vagus nerve stimulation. Described herein are methods and apparatuses that may be used to identify, e.g., responders from non-responders and/or low-responders.

SUMMARY OF THE DISCLOSURE

The present invention relates generally to systems and methods for using vagus nerve stimulation for treatment, and more specifically to screening tests for identifying suitable patients for vagus nerve stimulation treatment.

In general, described herein are method for screening a patient for responsiveness to vagus nerve stimulation by challenging an extracted blood sample from the patient (either fresh or frozen). Also descried herein are alternatively or additional methods for determining if a patient will respond to vagus nerve stimulation by comparing patient levels of a biomarker before and after vagus nerve stimulation. Surprisingly, techniques for examining extracted blood in the absence of vagus nerve stimulation may predict how well a patient may respond to vagus nerve stimulation, including in particular, vagus nerve stimulation to treat an inflammatory disorder using an implanted vagus nerve stimulator.

For example, described herein are methods of treating a patient having an inflammatory disorder with vagus nerve stimulation. In some variations, these methods may be methods of determining if a patient will respond (e.g., is a responder) or will not respond (e.g., is a non-responder) to vagus nerve stimulation and therefore should or should not have a vagus nerve stimulation device implanted. For example, a method of treating a patient having an inflammatory disorder with vagus nerve stimulation may include: challenging a sample of blood with a first concentration of toxin, wherein the sample is taken from the patient prior to implantation of a vagus nerve stimulator; challenging a second sample of blood with a second concentration of toxin that is at least 2 times (e.g., 3×, 4×, 5×, 6×, 7×, 8×, 9×, 10×, 15×, 20×, 25×, 30×, 50×, 100×, etc.) the first concentration, wherein the second sample is taken from the patient prior to implantation of the vagus nerve stimulator; and implanting the vagus nerve stimulator to treat the patient for the inflammatory disorder when an amount of an inflammatory cytokine released in response to the second concentration of toxin is greater than an amount of the inflammatory cytokine released in response to the first concentration of toxin by a threshold.

Any of these methods may include determining a ratio of the amount of the inflammatory cytokine released in response to the second concentration of toxin and the amount of the inflammatory cytokine released in response to the first concentration, and may compare this ratio to a threshold ratio (e.g., a cutoff threshold). For example, the threshold ratio for the change in inflammatory cytokine release due to increasing toxin amount may be, e.g., 50, 55, 60, 65, 70, 75, 80, 85, 90, 95, 100, etc. In some variations the threshold ratio is 60 (e.g., a patient is a good candidate if the ratio is greater than 60).

Any of the methods described herein may include displaying an indication that the patient is a responder or a non-responder based on the amount of the inflammatory cytokine released in response to the second concentration of toxin compared to the amount of the inflammatory cytokine released in response to the first concentration of toxin (including based on the ratio of the inflammatory cytokine release at different levels of toxin).

The methods described herein may include measuring the amount of the inflammatory cytokine that is released in response to the first concentration and measuring the amount of the inflammatory cytokine that is released in response to the second concentration.

As described in greater detail below, the toxin may be an endotoxin, including Lipopolysaccharide (LPS).

Although a first and a second level of toxin are described, one or more additional toxin levels may also be described, such as a third or fourth toxin challenge. For example, the method may include challenging a third sample of blood with a third concentration of toxin that is at least 2 times the second concentration, wherein the third sample is taken from the patient prior to stimulation of the patient's vagus nerve and wherein implanting the vagus nerve stimulator comprises implanting the vagus nerve stimulator when an amount of an inflammatory cytokine released in response to the third concentration of toxin is greater than an amount of the inflammatory cytokine released in response to the first and second concentrations of toxin by the threshold.

In some variations, challenging the second sample of blood with the toxin at the second concentration may comprises challenging with a concentration that is at least 10 times the first concentration.

In general, the first sample of blood and the second sample of blood may be portions of a master sample taken from the patient. Thus, the same blood sample may be challenged with different levels of toxin.

The inflammatory cytokine may be one or more of: tumor necrosis factor (TNF), interleukin-1 (IL-1), interleukin-6 (IL-6), interleukin-12 (IL-12), interleukin-18 (IL-18), inflammsome, interferon gamma, and granulocyte-macrophage colony stimulating factor. In some variations, the inflammatory cytokine may be TNF.

For example, a method of treating a patient having an inflammatory disorder with vagus nerve stimulation may include: obtaining a sample of blood taken from the patient prior to implantation of a vagus nerve stimulator; challenging the sample of blood with LPS at a first concentration of LPS; measuring a level of an inflammatory cytokine that is released in response to the LPS challenge at the first concentration of LPS; challenging the sample of blood with LPS at a second concentration of LPS that is at least 5 times the first concentration of LPS; measuring a level of the inflammatory cytokine that is released in response to the LPS challenge at the second concentration of LPS; determining a response curve based on the level of the inflammatory cytokine that is released in response to the LPS challenges at the first concentration of LPS and the second concentration of LPS; and implanting the vagus nerve stimulation when the determined response is greater than a cutoff threshold.

The second concentration of LPS may be at least 10 times the first concentration of LPS. The method may include challenging the sample of blood with LPS at a third concentration of LPS that is at least 5 times the second concentration of LPS, and wherein the response curve is determined based on the level of the inflammatory cytokine that is released in response to the LPS challenges at the first concentration of LPS, the second concentration of LPS, and the third concentration of LPS. The inflammatory cytokine may be selected from the group consisting of TNF, IL-1, IL-6, IL-12, IL-18, inflammsome, interferon gamma, and granulocyte-macrophage colony stimulating factor. For example, the inflammatory cytokine nat be TNF. The step of determining the response curve may include calculating a slope of the response curve. The method may include comprising comparing the determined response curve to the cutoff threshold by comparing a slope of the response curve to the cutoff threshold. Implanting may comprises determining whether a slope of the response curve is greater than the cutoff threshold.

The methods (and apparatuses for performing them) described herein may include in vitro methods for screening a patient for responsiveness to vagus nerve stimulation to treat an inflammatory disorder. For example, a method may include: challenging a sample of blood with a first concentration of toxin, wherein the sample is taken from the patient prior to stimulation of the patient's vagus nerve; challenging a second sample of blood with a second concentration of toxin that is at least 2 times the first concentration, wherein the second sample is taken from the patient prior to stimulation of the patient's vagus nerve; and outputting an indication that the patient is a responder or a non-responder for vagus nerve stimulation based on the amount of inflammatory cytokine released in response to the second concentration of toxin compared to the inflammatory cytokine released in response to the first concentration of toxin.

Any of these methods may include determining if the patient is a responder for vagus nerve stimulation by determining that a ratio of the amount of the inflammatory cytokine released in response to the second concentration of toxin and the amount of the inflammatory cytokine released in response to the first concentration of toxin is greater than a threshold ratio. For example, the threshold ratio may be greater than 60. Any of these methods may include challenging the sample of blood with the toxin at a third concentration that is at least 2 times the second concentration and measuring a level of the inflammatory cytokine that is released in response to the third concentration, wherein outputting the indication that the patient is a responder for vagus nerve stimulation treatment to treat an inflammatory disorder is based on the amount of inflammatory cytokine released in response to the third concentration of toxin relative to the response to the first and second concentrations of toxin.

Challenging the sample of blood with the toxin at a second concentration may comprise challenging with a concentration that is at least 10 times the first concentration.

An in vitro method for screening a patient for responsiveness to vagus nerve stimulation may include: obtaining a sample of blood taken from the patient prior to stimulation of the patient's vagus nerve; challenging the sample of blood with LPS at a first concentration of LPS; measuring a level of an inflammatory cytokine that is released in response to the LPS challenge at the first concentration of LPS; challenging the sample of blood with LPS at a second concentration of LPS that is at least 5 times the first concentration of LPS; measuring a level of the inflammatory cytokine that is released in response to the LPS challenge at the second concentration of LPS; and determining a response curve based on the level of the inflammatory cytokine that is released in response to the LPS challenges at the first concentration of LPS and the second concentration of LPS; comparing the determined response curve to a cutoff; and determining whether the patient is suitable for vagus nerve stimulation based on the comparison of the determined response curve to the cutoff.

The second concentration of LPS may be at least 10 times the first concentration of LPS. The method may also include challenging the sample of blood with LPS at a third concentration of LPS that is at least 5 times the second concentration of LPS, and wherein the response curve is determined based on the level of the inflammatory cytokine that is released in response to the LPS challenges at the first concentration of LPS, the second concentration of LPS, and the third concentration of LPS. The inflammatory cytokine may be selected from the group consisting of TNF, IL-1, IL-6, IL-12, IL-18, inflammsome, interferon gamma, and granulocyte-macrophage colony stimulating factor (e.g., TNF). The step of determining the response curve may include calculating a slope of the response curve. Comparing the determined response curve to the cutoff may include comparing the slope of the response curve to the cutoff.

Determining whether the patient is suitable for vagus nerve stimulation may include determining whether the slope of the response curve is greater than the cutoff.

Also described herein are methods that examine the levels of one or more biomarker(s) before and after an intentional vagal nerve stimulation (e.g., a mechanical and/or electrical stimulation of the vagus nerve). For example, a method for screening a patient for responsiveness to vagus nerve stimulation may include: measuring a baseline level of C-reactive protein (CRP) in a sample of blood taken from the patient; intentionally stimulating the vagus nerve (e.g., mechanically and/or electrically); measuring a post-stimulation level of CRP in a sample of blood taken after the vagus nerve has been stimulated; comparing the post-stimulation level of CRP to the baseline level of CRP; and indicating if the patient is a suitable candidate for an implantable vagus nerve stimulation device based on the comparison of the post-stimulation level of CRP to the baseline level of CRP.

Indicating may comprise indicating that the patient is a suitable candidate for the implantable vagus nerve stimulation device when the post-stimulation level of CRP increases by 5% or more.

The vagus nerve may be stimulated in any appropriate manner, including noninvasively, with transcutaneous electrical stimulation, by mechanical stimulation, stimulating the auricular branch of the vagus nerve, stimulating a cervical portion of the vagus nerve, or combinations of these. For example, any of these methods may include: introducing an electrode intravascularly via percutaneous puncture; and positioning the electrode at a cervically located blood vessel proximate the vagus nerve. In some variations the method may include introducing an electrode into the carotid sheath; and positioning the electrode within the carotid sheath such that the electrode is proximate the vagus nerve. The methods may include: placing an electrode of a transcutaneous electrical nerve stimulation device on the patient's skin over the cervical vagus nerve.

For example, a method of treating a patient having an inflammatory disorder with vagus nerve stimulation may include: measuring a baseline level of C-reactive protein (CRP) in a sample of blood taken from the patient; stimulating the patient's vagus nerve; measuring a post-stimulation level of CRP in a sample of blood taken after the vagus nerve has been stimulated; comparing the post-stimulation level of CRP to the baseline level of CRP; and implanting a vagus nerve stimulator if the patient is a suitable candidate for an implantable vagus nerve stimulation device based on the comparison of the post-stimulation level of CRP to the baseline level of CRP.

A method for screening a patient for responsiveness to vagus nerve stimulation may include: measuring a baseline level of a cytokine and one or more of lymphocytes and monocytes in a sample of blood taken from the patient; stimulating the vagus nerve; measuring a post-stimulation level of the cytokine and the one or more of lymphocytes and monocytes in a sample of blood taken after the vagus nerve has been stimulated; comparing the post-stimulation level of the cytokine and the one or more of lymphocytes and monocytes to the baseline level of the cytokine and the one or more of lymphocytes and monocytes; and indicating if the patient is a suitable candidate for an implantable vagus nerve stimulation device based on the comparison of the post-stimulation levels of the cytokine and the one or more of lymphocytes and monocytes to the baseline levels of the cytokine and the one or more of lymphocytes and monocytes.

The cytokine may comprise interleukin 7 (IL-7) and the one or more of lymphocytes and monocytes comprise CD3−CD19+ cells (e.g., cells recognized by the well-known CD3 antibody recognize some human T lymphocyte, and CD19 antibody recognizes human B lymphocytes).

Indicating may comprise indicating a patient is a responder if the patient indicated an increase or a decrease of 10% or less (e.g., 10% or less, 9% or less, 8% or less, 7% or less, 6% or less, 5% or less, 4% or less, 3% or less, 2% or less, 1% or less, etc., less than 10%, etc.) in the cytokine and the one or more of lymphocytes and monocytes compared to baseline. Indicating may comprise indicating that the patient is a non-responder if the cytokine and the one or more of lymphocytes and monocytes exhibited a greater than 10% (e.g., greater than 11%, greater than 12%, greater than 13%, greater than 14%, greater than 15%, greater than 20%, greater than 25%, etc.) decrease in CD3−, CD19+(e.g., B-lymphocytes) cell populations and a greater than 10% decrease in IL-7 levels compared to baseline. The method vagus nerve may be stimulated noninvasively, and/or with transcutaneous electrical stimulation, and/or by mechanical stimulation, and/or by stimulating the auricular branch of the vagus nerve, and/or by stimulating a cervical portion of the vagus nerve, etc. For example, the method may include introducing an electrode intravascularly via percutaneous puncture; and positioning the electrode at a cervically located blood vessel proximate the vagus nerve. The method may include introducing an electrode into the carotid sheath; and positioning the electrode within the carotid sheath such that the electrode is proximate the vagus nerve. The method may include: placing an electrode of a transcutaneous electrical nerve stimulation device on the patient's skin over the cervical vagus nerve.

Also described herein are methods of treating a patient having an inflammatory disorder with vagus nerve stimulation, the method comprising: measuring a baseline level of a cytokine and one or more of lymphocytes and monocytes in a sample of blood taken from the patient; stimulating the vagus nerve; measuring a post-stimulation level of the cytokine and the one or more of lymphocytes and monocytes in a sample of blood taken after the vagus nerve has been stimulated; comparing the post-stimulation level of the cytokine and the one or more of lymphocytes and monocytes to the baseline level of the cytokine and the one or more of lymphocytes and monocytes; and implanting a vagus nerve stimulator if the patient is a suitable candidate for an implantable vagus nerve stimulation device based on the comparison of the post-stimulation level of the cytokine and the one or more of lymphocytes and monocytes compared to the baseline level of the cytokine and the one or more of lymphocytes and monocytes.

For example, described herein are methods for screening a patient for responsiveness to vagus nerve stimulation comprising all of some of the following steps: obtaining a sample of blood taken from the patient prior to application of vagal nerve stimulation of the patient; challenging the sample of blood with an agent that evokes an immune response, e.g., a toxin or particularly an endotoxin, such as Lipopolysaccharides (LPS), at a first concentration; measuring a level of an inflammatory cytokine that is released in response to the challenge at the first concentration; challenging the sample of blood with the same or a different toxin (and particularly an endotoxin such as LPS) at a second concentration that is higher than the first concentration (e.g., at least twice, 3×, 4×, 5×, 6×, 7×, 8×, 9×, 10×, 11×, 15×, 20×, 25×, 30×, etc.); measuring a level of the inflammatory cytokine that is released in response to the second challenge at the second concentration; and determining if the patient is suitable for vagus nerve stimulation based on the response to the second challenge relative to the first challenge. For example, determining if the patient is suitable for vagus nerve stimulation may be based on a response curve of the level of the inflammatory cytokine that is released in response to the challenges at the first concentration (e.g. of LPS) and the second concentration (e.g., of LPS), and comparing the determined response curve to a threshold.

For example, when the challenge is an LPS challenge, the second concentration of LPS may be at least 10 times the first concentration of LPS.

Any of these methods may also include challenging the sample of blood with a third concentration of toxin (e.g., endotoxin such as LPS) that is at twice (e.g., at least 2×, 3×, 4×, 5×, 6×, 7×, 8×, 9×, 10×, 11×, 12×, 15×, 20×, 25×, 30×, etc.) the second concentration, and wherein the fitness for vagal nerve stimulation is determined based on the level of the inflammatory cytokine that is released in response to the third challenges relative to the first and/or second challenge concentrations.

In any of the methods described herein, the inflammatory cytokine examined from the blood sample may be one or more of: TNF, IL-1, IL-6, IL-12, IL-18, inflammsome, interferon gamma, and granulocyte-macrophage colony stimulating factor. The inflammatory cytokine may be TNF.

In any of these example, a response curve may be determined. For example, determining a response curve may include calculating a slope of the response curve. The determined response curve may be compared to a cutoff, e.g., by comparing the slope of the response curve to the cutoff.

Determining whether the patient is not suitable for vagus nerve stimulation may include determining whether the slope of the response curve is less than the cutoff.

In general, the methods described herein may be performed on blood ex vivo; the blood sample may be withdrawn from the patient and stored (e.g., frozen, etc.) or used fresh, and challenged over time or simultaneously with multiple levels of toxin (e.g., endotoxin). This may allow the patient to be screened without any associated risk to the patient, prior to any surgical intervention, including implanting a neurostimulator (vagus stimulator).

For example, venous blood may be drawn from the patient, an anticoagulant (e.g., heparin) added, and the blood may be aliquoted to tubes. Thereafter a toxin (endotoxin, such as LPS) may be mixed with the blood to final concentrations, e.g., of 0, 1, 10, and 100 ng/mL; the blood may be incubated, e.g., for 4 hr at 37° C. The plasma may be separated and an immune response (e.g., TNF level) measured, e.g., by ELISA.

Also described herein are methods of screening patient based on comparing a response of an inflammatory marker (e.g., C-reactive protein, CRP) before and after vagal nerve stimulation. Vagal nerve stimulation (VNS) may be performed anywhere on the vagus nerve, or and/or an associated nucleus. For example, VNS may be performed by transcranial stimulation to nucleus tractus solitarius (NTS), dorsal motor nucleus of the vagus (DMV), or Locus coeruleus (LC), for example.

For example, a method for screening a patient for responsiveness to vagus nerve stimulation may include: measuring a baseline level of CRP in a sample of blood taken before the vagus nerve has been stimulated; stimulating the vagus nerve after the step of measuring the baseline level of CRP; measuring a post stimulation level of CRP in a sample of blood taken after the vagus nerve has been stimulated; comparing the post stimulation level of CRP to the baseline level of CRP; and determining whether the patient is a suitable candidate for an implantable vagus nerve stimulation device based on the post-stimulation level of CRP relative to the baseline level of CRP. The stimulation of the vagus nerve may be done noninvasively. The vagus nerve stimulation may be done with transcutaneous electrical stimulation. The vagus nerve stimulation may be done with mechanical stimulation. The step of stimulating the vagus nerve may comprise stimulating the auricular branch of the vagus nerve. The stimulation of the vagus nerve may comprise stimulating a cervical portion of the vagus nerve.

For example, the method may include introducing an electrode intravascularly via percutaneous puncture; and positioning the electrode at a cervically located blood vessel proximate the vagus nerve.

The method may include introducing an electrode into the carotid sheath; and positioning the electrode within the carotid sheath such that the electrode is proximate the vagus nerve. Alternatively or additionally, the method may include placing an electrode of a transcutaneous electrical nerve stimulation device on the patient's skin over the cervical vagus nerve.

Any of the pre-screening methods described herein may also include one or more of: administration of nicotinic agonist, for example, a nicotinic a7 agonists, and/or one or more cholinesterase inhibitor(s).

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4A-4C illustrate that that there was no obvious or significant difference in LPS-induced TNF levels under various LPS concentrations between European League Against Rheumatism (EULAR) criteria responders and non-responders in the two cohorts of patients tested.

FIG. 12 is a table that shows changes in cell populations and IL-7 levels between screening day and after implantation of the vagus nerve stimulation device.

FIG. 13 is a table that shows changes in cell populations and IL-7 levels between screening day and after implantation of the vagus nerve stimulation device.

DETAILED DESCRIPTION

Figure 1A:
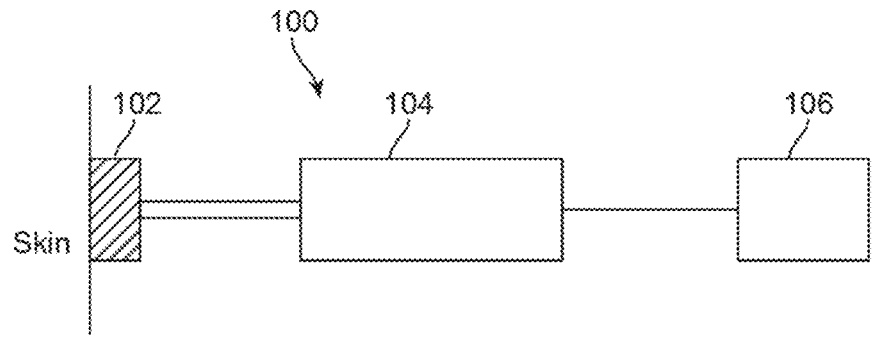
FIGS. 1A-1C illustrate various embodiments of a mechanical stimulator.

In general, described herein are methods and apparatuses for determining, e.g., by a blood test, if a subject (e.g., a mammalian, including human, patient) will benefit and/or respond to electrical and/or mechanical vagus nerve stimulation (VNS) in order to treat an inflammatory disorder.

In particular, described herein are methods and apparatuses (devices, systems, assays, etc.) for taking a blood sample from a patient and performing one or more procedures on the blood sample, without having to subject the patient to any stimulation. This may allow for the identification of patients that may benefit from the therapy (or may require additional or adjunctive therapies or modifications in the level of therapy provided) prior to providing any therapy to the patient. Since the methods may be performed just on an ex vivo sample removed from the patient's body, the patient may be spared any risk, complications, and/or discomfort due to stimulation.

Described herein are three variations of the ex vivo methods for determining if a patient will respond to vagus nerve stimulation. For example, described herein are methods for treatment of Rheumatoid Arthritis (RA) by activating the CAP using electrically active implantable medical devices; these methods may include first confirming that the patient is a candidate for treatment using any of the methods described herein.

For example, a study of vagus nerve stimulation (VNS) using an electrically active surgically implanted medical device in 8 patients with active rheumatoid arthritis (RA) was performed at 4 investigative centers. The device used an implanted helical coiled cuff lead to deliver electrical stimulation from an implanted pulse generator. After 6 weeks of stimulation, clinically significant improvements were seen in 6 of 8 patients as assessed by standard RA efficacy outcome measures such as the Disease Activity Score (DAS). These results provide proof-of-concept for the therapeutic use of VNS in RA as an alternative to small molecule and biological agent therapy. However, while the majority of the patients in the study responded, 2 of 8 did not have a meaningful clinical response. In order for VNS to be more successful as a therapy, it would be desirable to use a diagnostic screening test to preoperatively predict likelihood of clinical response to an implant, thus sparing patients who are unlikely to respond from undergoing an unnecessary surgical procedure. The diagnostic screening tests described herein may utilize various techniques, such as mechanical and electrical stimulation to stimulate the vagus nerve noninvasively and/or in some cases an iv vitro toxin challenge, to determine if a patient will respond to treatment prior to implantation of the electrical stimulation.

For example, in some variations, the effectiveness of CAP Activation may be determined by stimulation of the auricular branch of the vagus verve prior to implantation. Sensory fibers of the Auricular Branch of the Vagus Nerve (ABVN) innervate the skin of the cymba concha of the external ear. These fibers may provide afferent input via the superior ganglion of the vagus to the brainstem nucleus of the solitary tract (NST). The neurons of the NST then project to efferent neurons originating in the dorsal nucleus and nucleus ambiguous of the vagus nerve, which then in turn project within the vagus nerve to the visceral organs.

This neuroanatomical pathway may provide a potential mechanism for non-invasive activation of the CAP by induction of efferent vagal outflow through stimulation of the afferent ABVN pathway using mechanical or electrical stimulation of the skin of the cymba concha. The ABVN is particularly suitable for noninvasive stimulation because the nerves are located relatively close to the surface of the skin. Similarly, other portions of the vagus nerve that are similarly situated close to the patient's skin may be used for noninvasive stimulation. For example, the nerve may be located less than about 2, 1, 0.5 or 0.25 cm from the surface of the patient's skin. The terms "about", "approximately" and the like can mean within 10%, 20%, or 30%.

The presence of such a functional reflex pathway (immune reflex pathway) in the ABVN is suggested by the following observations: (1) the "Arnold's reflex" occurs in approximately 2% of the population and results in coughing or gagging in response to mechanical stimulation of the ear canal; (2) ABVN electrical stimulation in rats resulted in parasympathetic vagally-mediated reductions in heart rate and blood pressure, and increased intra-gastric pressure. This response could be abrogated with atropine; (3) ABVN electrical stimulation in dogs reverses the acute right atrial remodeling and reduction in threshold for inducible atrial fibrillation caused by rapid right atrial pacing; and this protective effect of ABVN could be eliminated by bilateral transection of the vagus in its upper thoracic segment; (4) the ability of ABVN stimulation to activate the CAP and inhibit systemic inflammation in rodents. In a rodent systemic endotoxemia model, transcutaneous electrical ABVN stimulation was compared to VNS delivered using a surgically placed cervical electrode. While cervical VNS was the most effective, ABVN stimulation caused significant reductions in circulating tumor necrosis factor (TNF), Interleukin (IL)-1 beta, and IL-6, thus demonstrating that the CAP can be effectively activated by transcutaneous auricular stimulation.

Described herein are methods and apparatuses for using the CAP activation as a diagnostic screening test by applying a short duration stimulation of the skin of the external ear, for example either mechanically or with an electric current. The stimulation duration can be between about 1 second to 24 hours and can be applied either continuously or intermittently throughout the duration. In some embodiments, the duration is less than about 1, 5 10, 20, 30, or 60 seconds. In some embodiments, the duration is less than about 1, 2, 3, 4, 5, 10, 15, 20, 30, 40, 50, or 60 minutes. In some embodiments, the duration is less than about 1, 2, 3, 4, 5, 6, 12, 18, or 24 hours.

The non-invasive stimulation may include mechanical stimulation of a body region such as the subject's ear. Examples of non-invasive stimulation devices are described in U.S. Publication No. 2008/0249439 to Tracey et al., which is herein incorporated by reference in its entirety. In particular, the cymba conchae region of their ear may be stimulated. The non-invasive stimulation may comprise mechanical stimulation between about 1 and 500 Hz, or 30 Hz and 500 Hz, or 50 Hz and 500 Hz. In some variations the stimulation is transcutaneous stimulation applied to the appropriate body region (e.g., the ear). For example, transcutaneous stimulation may be applied for an appropriate duration (e.g., less than 24 hours to less than 1 hour, less than 60 minutes to less than 1 minute, less than 60 seconds to less than 1 second, etc.), at an appropriate intensity and frequency. Stimulation that does not significantly affect cardiac measures may be particularly desirable, and the stimulation may be limited to such a range, or may be regulated by cardiac feedback (e.g., ECG, etc.).

Figure 1B:
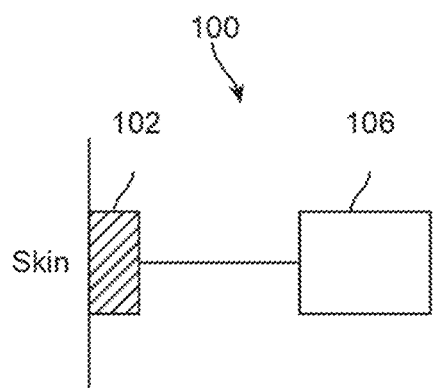
Figure 1C:
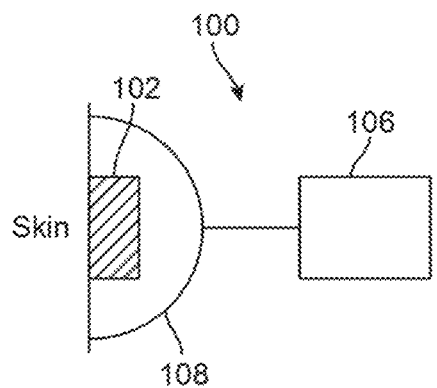

Also described herein are devices for non-invasively mechanically stimulating a subject's inflammatory reflex, as illustrated in FIGS. 1A-1C. These mechanical stimulation devices 100 may include an actuator 102, such as a movable distal tip region that is configured to mechanically stimulate at least a portion of a subject's ear, a handle 104, and a driver 106 configured to move the distal tip region between about 50 and 500 Hz. In some variations, the stimulation devices are part of a system including a stimulation device. In some embodiments, the actuator 102 can be directly adhered to the patient's skin, thereby removing the need for a handle. The actuator 102 can be coated with an adhesive or can be integrated into an adhesive pad or pod 108.

A stimulation device may include a controller configured to control the driver so that it applies stimulation within stimulation parameters. For example the controller (which may be part of the driver, or may be separate from the driver) may control the intensity (e.g., force, displacement, etc.), the timing and/or frequency (e.g., the frequency of repeated pulses during a stimulation period, the stimulation duration during the period of stimulation, the duration between stimulation periods, etc.), or the like. In some variations the controller is pre-programmed. In some variations, the controller receives input. The input may be control input (e.g., from a physician or the patient) that modifies the treatment. In some variations the stimulator device includes a therapy timer configured to limit the duration of stimulation. For example, the controller may be configured to limit the period of stimulation to less than 10 minutes, less than 5 minutes, less than 3 minutes, less than 1 minute, etc.

Any appropriate driver may be used. For example, the driver may be a motor, voice (or speaker) coil, electromagnet, bimorph, piezo crystal, electrostatic actuator, and/or rotating magnet or mass. For example, in some variations the driver is a mechanical driver that moves an actuator against the subject's skin. Thus, an actuator may be a distal tip region having a diameter of between about 35 mm and about 8 mm.

In some variation the stimulator includes a frequency generator that is in communication with the driver. Thus the driver may control the frequency generator to apply a particular predetermined frequency or range of frequencies to the actuator to non-invasively stimulate the subject.

The stimulator devices described herein may be hand-held or wearable. For example, also described herein are wearable device for non-invasively stimulating a subject's inflammatory reflex. These stimulator the devices may include an actuator configured to mechanically stimulate a subject's cymba conchae, a driver configured to move the distal tip region between about 1 and 500 Hz, or 30 Hz and 500 Hz, or 50 Hz and 500 Hz, and an ear attachment region configured to secure to at least a portion of a subject's ear.

Figure 2:
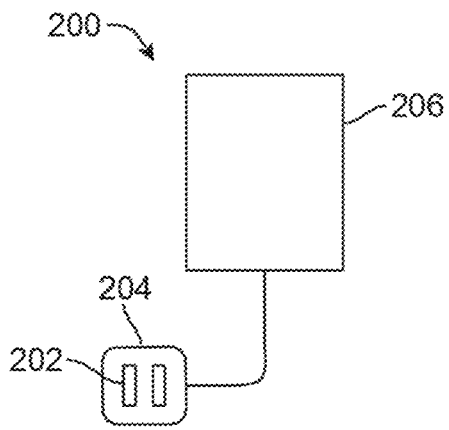
FIG. 2 illustrates an embodiment of a transcutaneous electrical nerve stimulation device.

Transcutaneous electrical nerve stimulation (TENS) can be provided by an electrical stimulation device 200 having at least one electrode 202 that can be placed on the patient's skin, as illustrated in FIG. 2. The electrode 202 can be integrated into an adhesive patch or pad 204 that can be adhered to the patient's skin. A lead can connect the electrode with the housing 206 of the device. Alternatively, the housing can also be integrated with the adhesive patch or pad. A control or signal generator can deliver the electrical signal stimulus through the electrode. The signal amplitude can be between about 0.05 to 10 mA, or 0.05 to 15 mA, or 0.05 to 20 mA, or 0.05 to 25 mA, or 0.05 to 50 mA. The pulse width can be between about 100 and 1,000 µS. The pulse frequency can be between about 1 and 50 Hz, and the stimulus duration can be between about 1 second and 24 hours.

The electrical parameters can be similar when the electrical stimulation is provided by an electrode that has been inserted into the patient through minimally invasive techniques as described herein. For example, the signal amplitude can be between about 0.05 to 5 mA, or 0.05 to 10 mA, or 0.05 to 15 mA, 0.05 to 20 mA, or 0.05 to 25 mA or 0.05 to 50 mA.

Figure 3A:
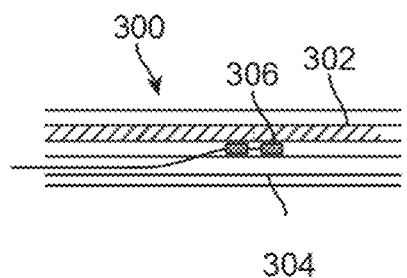
FIGS. 3A-3C illustrate various embodiments of minimally invasive electrical stimulation of the vagus nerve.
Figure 3B:
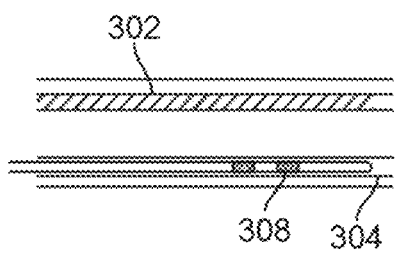
Figure 3C:
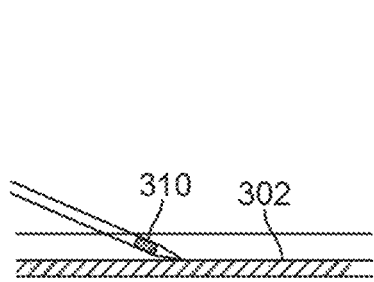

In some variations a method for treating a patient and/or determining if a patient is a candidate for treatment may include CAP activation by stimulation of the cervical vagus nerve. These methods may include acutely invasive techniques. For example, temporary electrical stimulation of the cervical vagus nerve for screening purposes can be performed using a variety of devices. A device can include a non-cuffed lead 306 placed percutaneously through a blood vessel 304 such as the internal jugular vein on or near the vagus nerve 302 within the carotid sheath 300, as illustrated in FIG. 3A. Alternatively, as shown in FIG. 3B, a standard percutaneous catheter-directed intravascular electrode 308 can be positioned within the internal jugular 304 or other nearby blood vessel, in close anatomical apposition to the vagus nerve 302, with electrical stimulation delivered transvascularly. Other electrode or lead configurations, such as needle electrodes 310, can also be used to temporarily stimulate the vagus nerve 302, as shown in FIG. 3C.

Figure 3D:
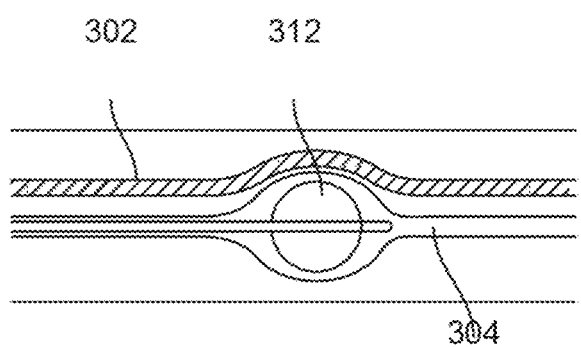
FIG. 3D illustrates an embodiment of minimally invasive mechanical stimulation of the vagus nerve.

Alternatively, direct mechanical stimulation of the cervical vagus nerve by physical manipulation has been demonstrated to activate the CAP in the rodent endotoxemia model. Angioplasty of the internal jugular vein may be performed using percutaneously inserted balloon-tipped angioplasty catheters. Transmural pressure can be exerted internally within the internal jugular vein 304 using such balloon catheters 312 in order to mechanically stimulate the nearby cervical vagus nerve 302 and activate the CAP, as shown in FIG. 3D. Other mechanical stimulators or expanders can also be used to provide mechanical stimulation.

Alternatively, the cervical vagus nerve can also be stimulated using intravascular or transcutaneous ultrasound, transcutaneous magnetic energy, transcutaneous RF energy, and transcutaneous electric stimulation.

The CAP can be activated in the diagnostic screening test described herein by short duration (1 second to 24 hour) stimulation of the cervical vagus nerve using the above methods, either mechanically or with an electric current.

Furthermore, in some variations, CAP activation specific to a patient may be examined using a bioassay performed on one or more peripheral blood samples. The degree of CAP activation induced by the stimulation methods described above can be measured in a diagnostic screening test using several biological activity assays performed on either serum samples, supernatants from whole blood samples cultured in vitro in the presence of cytokine release stimulators, or supernatants from separated cellular constituents of whole blood cultured in vitro in the presence of cytokine release stimulators. Alternatively or additionally, the assay may be based on tissue samples or other biological fluids. The reduction or increase in these mediators that is observed between a pre-stimulus measurement and a post-stimulus measurement, and/or between stimulation at different levels, may be indicative of the responsiveness of the patient to CAP activation, and may predict the response to a permanently implanted VNS system. For example, a predetermined change in level or concentration of a mediator, cytokine, or analyte from a baseline level or concentration before stimulation may indicate responsiveness of the CAP to stimulation and suitability of the patient for an implanted VNS system. Alternatively, the reduction or increase in inducible release of a cytokine, mediator, signaling molecule, or other analyte in a cell-based assay can also be used. In some embodiments, the predetermined change is a reduction of at least 10, 20, 30, 40 or 50%. In some embodiments, the predetermined change is an increase of at least 10, 20, 30, 40 or 50%.

For example, one bioassay measures endotoxin, e.g., lipopolysaccharide (LPS), induced TNF levels in whole blood samples taken during the screening day before implantation of the VNS stimulator or before any stimulation of the vagus nerve. FIGS. 4A-8 illustrate one set of experiments characterizing an in vitro assay in which blood samples from both responders and non-responders (taken before implantation) were compared. To perform the whole blood assay (WBA), venous blood was drawn from each patient and dispensed with heparin into separate tubes on a screening day (e.g., day −21). LPS (endotoxin) was mixed with the blood to final concentrations of 0, 1, 10, and 100 ng/mL. Blood was incubated for 4 hours at 37° Celsius. Plasma was then separated from the whole blood and TNF levels were measured by ELISA. On Day −14, seven days after the screening day, the patients were then implanted with a cervical vagus nerve stimulation device for treatment of inflammation caused by rheumatoid arthritis, and on Day 0, two weeks after implantation the vagus nerve was stimulated with the implanted device and subsequently stimulated according to a prescribed therapy regimen. The patients were characterized as responders or nonresponders based on their response to the VNS therapy. The screening test data was then analyzed.

FIGS. 4A-4C illustrate that there was no obvious or significant difference in LPS-induced TNF levels under various LPS concentrations between European League Against Rheumatism (EULAR) criteria responders and non-responders in the two cohorts of patients tested. No difference is seen because the amount of TNF produced appears to be highly patient specific.

Figure 5:
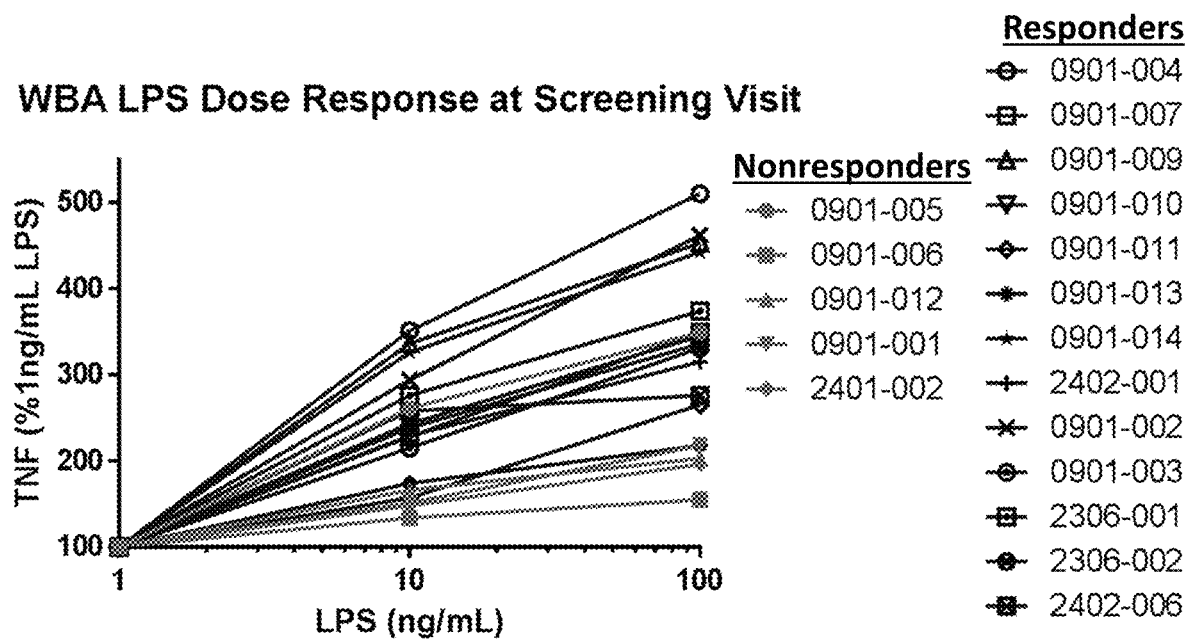
FIG. 5 illustrates LPS dose response curves for responders and nonresponders using blood samples before vagus nerve stimulation.
Figure 6:
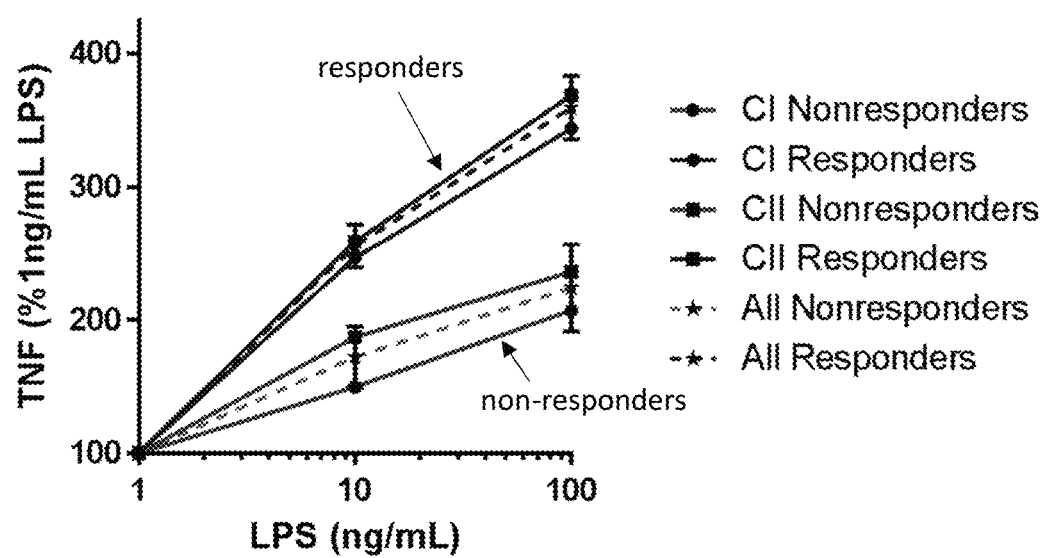
FIG. 6 illustrates LPS dose response curves for responders and nonresponders using blood samples before vagus nerve stimulation.
Figure 7:
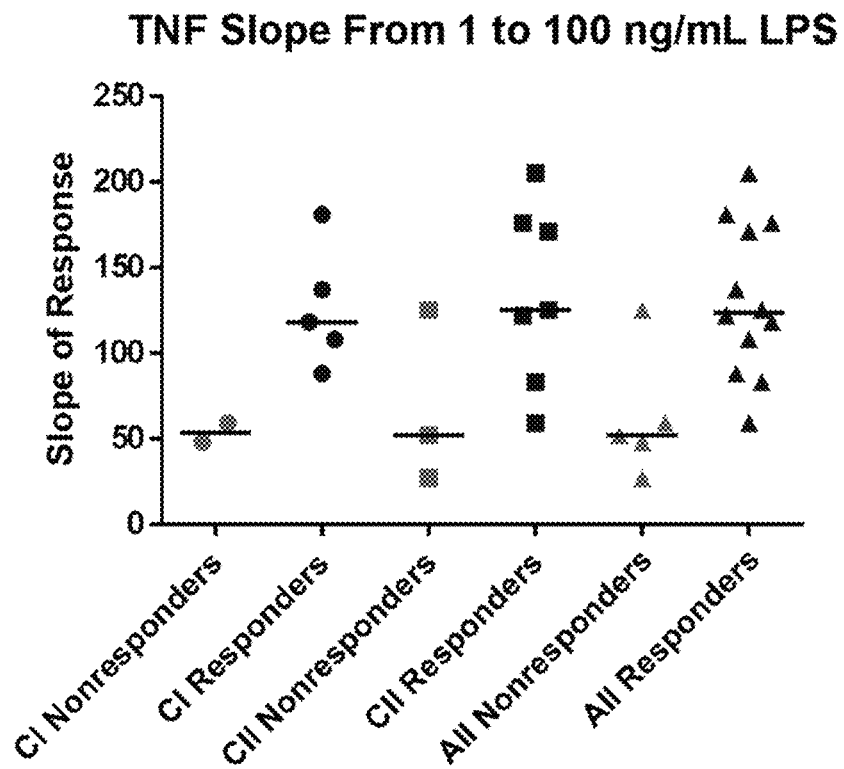
FIG. 7 illustrates the slopes of the LPS dose response curves for responders and non-responders to 100 ng/ml LPS.
Figure 8:
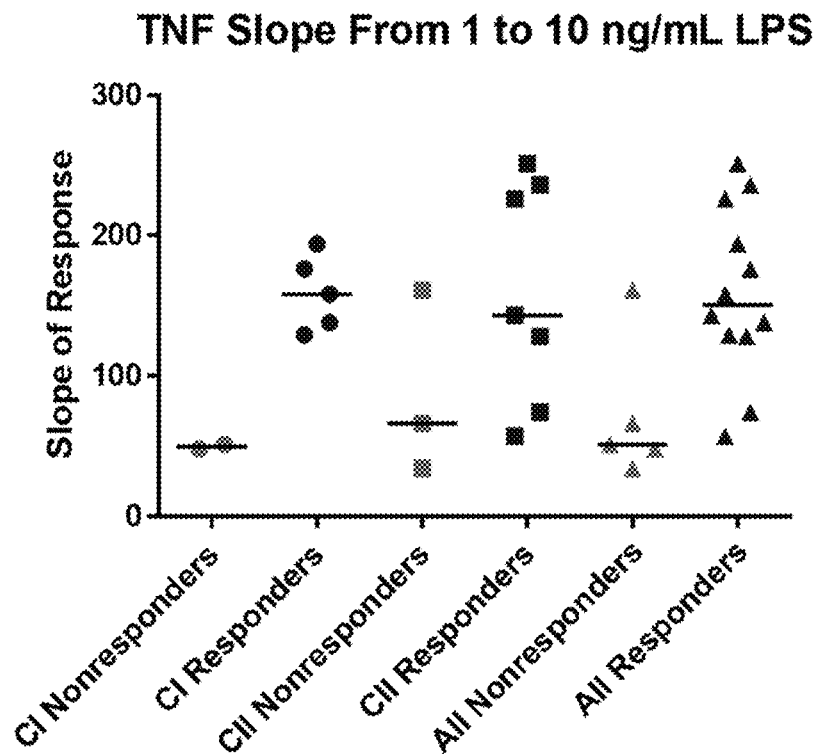
FIG. 8 illustrate the slopes of the LPS dose response curves for responders and non-responders to 10 ng/ml LPS.

However, a response curve analysis of the TNF level data surprisingly was able to identify and/or separate four out of five nonresponders from the two cohorts of patients (18 patients total—5 nonresponders and 13 responders) with a high level of significance. To perform the response curve analysis, patient-specific TNF levels produced at various LPS concentrations were normalized to TNF levels at 1 ng/mL LPS. Normalized TNF levels produced as a function of LPS concentration was plotted by individual and EULAR response, as shown in FIG. 5, and by cohort and EULAR response, as shown in FIG. 6. Slopes of the response curves were calculated, grouped, and plotted, as shown in FIGS. 7 and 8. For two patients, there was undetectable levels of TNF at 1 ng/mL LPS, so the slopes were extrapolated from the change between 10 and 100 ng/mL LPS.

Based on the data presented in FIG. 7 which presents TNF response data over a 3 log LPS concentration range (1 to 100 ng/mL LPS challenge), 4 of the 5 nonresponders had a slope of less than about 60 while all but one responder had a slope greater than about 60. Similarly, FIG. 8 presents TNF response data over a 2 log LPS concentration range (1 to 10 ng/mL LPS challenge), where 4 out of 5 nonresponders had a slope less than about 75 while all but two responders had a slope greater than about 75.

FIGS. 7 and 8 demonstrate that a screening test based on an assay that measures TNF release or release of another inflammatory cytokine, such as IL-1, IL-6, IL-12, IL-18, inflammsome, interferon gamma, and granulocyte-macrophage colony stimulating factor, from blood cells, particularly white blood cells, in response to LPS/endotoxin challenge over a range of LPS/endotoxin concentrations, can be used to effectively screen patients before implantation to determine whether a candidate is likely to respond or not respond to VNS therapy. In other words, an assay, such as a whole blood assay, that measures a response curve or response over range of challenge concentrations can be used as a screening test. In some embodiments, the range of concentration for the LPS/endotoxin can be at least 2, 3, or 4 logs, where 2 logs means that the highest concentration is 10 times the lowest concentration, and 3 longs means that the highest concentration is 100 times the lowest concentration. In some embodiments, the concentrations may be increased in multiples of at least 2, 3, 4, 5, 6, 7, 8, 9, or 10 times. The screening test can have a cutoff value for the response curve, such as the slope of the response curve or another measure of the degree or magnitude of the response over the concentration range, that establishes whether a candidate is suitable for VNS therapy. In some embodiments, the WBA can be performed using a commercial blood testing kit, such as a TruCulture® kit sold by Myriad RBM. In some embodiments, the blood can be incubated for less than 4 hours, such as less than 3, 2, or 1 hour, or incubation can be greater than 1, 2, 3, or 4 hours. In some embodiments, the assay can use whole blood, or it can use isolated white blood cells or monocytes. In some embodiments, the cells can be stimulated by LPS/endotoxin, while in other embodiments, other stimuli can be used to stimulate the blood cells. In some embodiments, the LPS/endotoxin concentration can range from about 1 ng/mL to about 100 ng/mL. In other embodiments, the low end for the LPS/endotoxin concentration can be less than 1 ng/mL, such as about 100 pg/mL or 10 pg/mL, and the high end can be about 1000 ng/mL or 10000 ng/mL.

Figure 9:
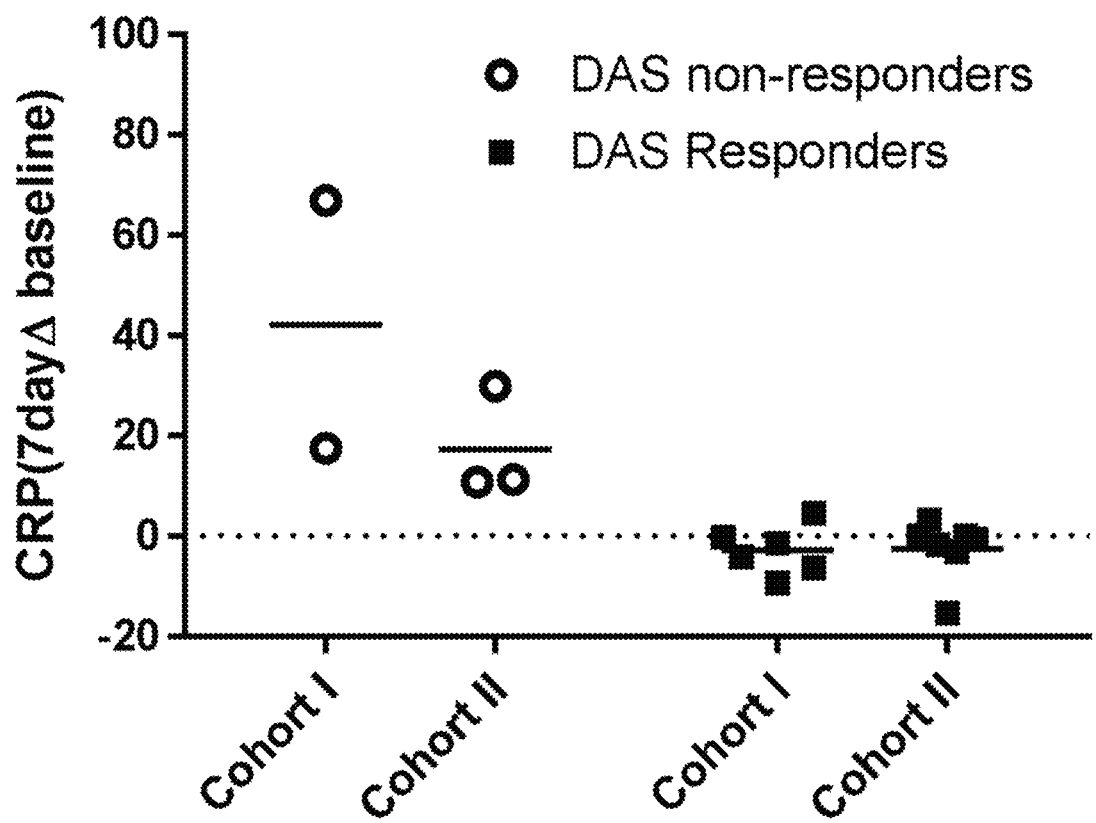
FIG. 9 illustrates the change in CRP levels after vagus nerve stimulation comparing responders and nonresponders.
Figure 10:
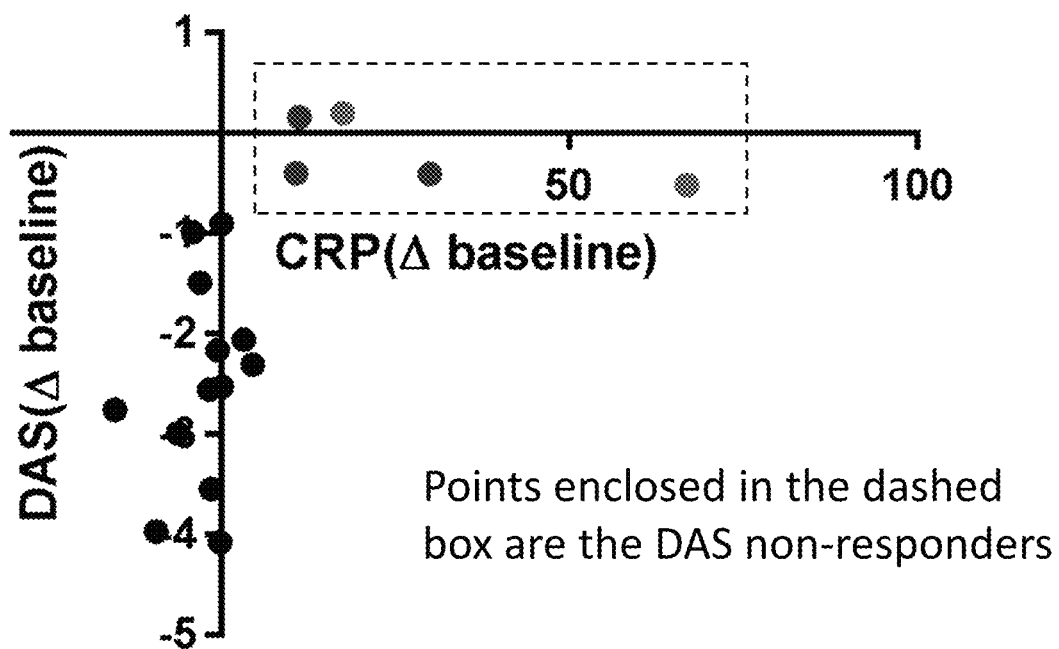
FIG. 10 illustrates the change in CRP levels after vagus nerve stimulation for responders and nonresponders (based on the change from baseline).
Figure 11:
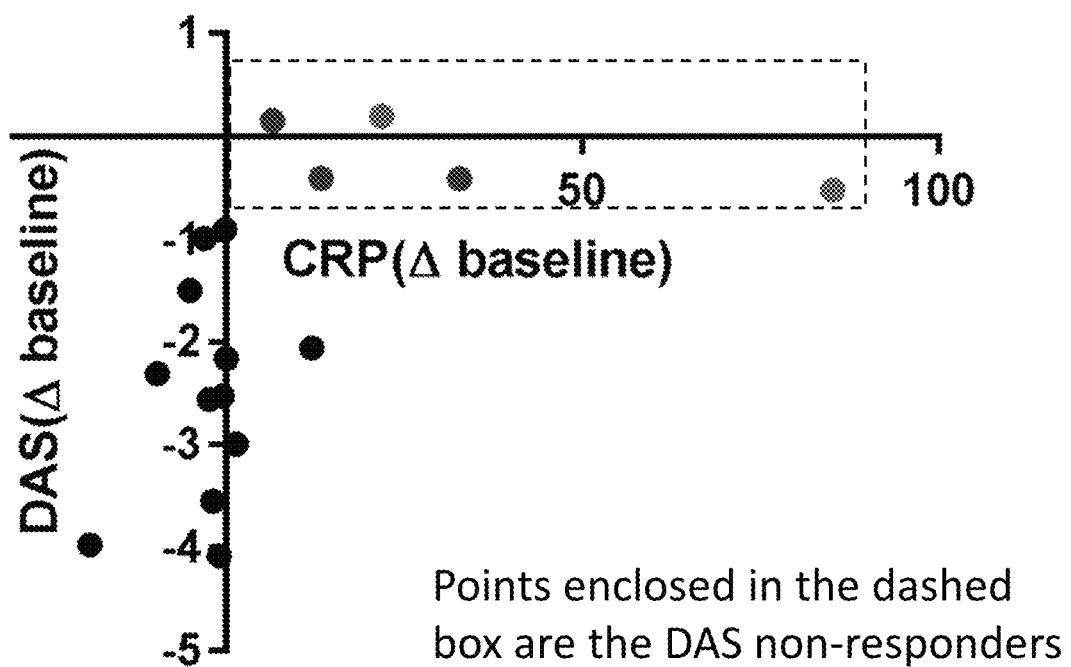
FIG. 11 illustrates another example of the change in CRP levels after vagus nerve stimulation for responders and nonresponders (based on the change from baseline).

Other tests may be performed after stimulation of the vagus nerve using noninvasive or minimally invasive devices. For example, C-reactive protein (CRP) is a protein synthesized in the liver and secreted into the blood in response to inflammation, particularly in response to IL-6 secretion by macrophages and T-cells. The prospective patient's blood can be collected during the screening day and again after the patient's vagus nerve has been stimulated noninvasively or minimally invasively. After a set or predetermined amount of time after VNS, such as 1, 2, 3, 4, 5, 6, 7, 8, 9, 10, 11, 12, 13, or 14 days, the second blood sample can be collected and both samples can be tested for a biomarker, such as CRP. The first sample taken before VNS stimulation can establish a baseline or reference level of the analyte of interest, and the second blood sample can establish the effect of VNS stimulation on the biomarker. For patients that are likely to respond well to VNS therapy, the CRP levels are likely to remain stable or be reduced, while patients that do not respond well to VNS therapy may show elevated levels of CRP, which may indicate worsening of inflammation. Therefore, patients that do not respond well to VNS therapy may be identified and excluded by setting a cutoff or threshold value based on a comparison of the CRP levels in the second sample to the reference CRP level, as shown in FIGS. 9-11, which show the change in CRP levels at Day 7 (seven days after initial VNS stimulation) with respect to a baseline level for responders and nonresponders (identified at Day 42 using EULAR criteria). For example, the data shown in FIGS. 9-11 indicate that the CRP levels of all the nonresponders increased by at least about 5 to 10 percent relative to the reference CRP level. Therefore, the cutoff for excluding patients can be an increase in CRP levels of greater than 5, 6, 7, 8, 9, 10, 11, 12, 13, 14, or 15 percent after VNS (e.g., non-invasive VNS or acutely invasive VNS).

FIGS. 12 and 13 present changes in cell populations and IL-7 levels from D-21 (screening day) to D0 (14 days after implantation of VNS device but before delivering any stimulation). All nonresponders exhibited greater than 10% decrease in CD3−CD19+(B-lymphocytes) cell populations and greater than 10% decrease in IL-7 levels (see FIG. 13).

Thus a method of treating a patient may include determining if the patient will respond to the treatment based on the relationship of one or more monocyte and lymphocyte populations after a transcutaneous vagus nerve stimulation during screening, particularly in combination with a biomarker such as an inflammatory marker (e.g., IL-7) by comparing the level of the monocytes and/or lymphocytes and the level of the inflammatory biomarker from a baseline taken prior to any treatment with a level following a non-invasive or acutely invasive treatment. In particular, if the level of the monocytes and/or lymphocytes (e.g., CD3−, CD19+ B-lymphocytes) and the level of the cytokine (e.g., IL-7) both decrease, the patient may be a non-responder, and implantation may be avoided. In patients for whom either or both the level of monocytes and/or lymphocytes (e.g., CD3−, CD19+ B lymphocytes) and the level of the cytokine (e.g., IL-7) increase between baseline and non-invasive or acutely invasive stimulation (which may be performed immediately prior to implantation), implantation may be completed as they are likely to respond to treatment.

Diagnostic Screening Tests

A diagnostic screening test can predict the likelihood of clinical response to the VNS implant prior to actual implantation surgery (or completion of implantation), for use in clinical decision-making regarding patient selection. Patients that are in need of or that may benefit from a VNS implant can be identified and given the diagnostic screening test. In some embodiments, the test is performed prior to implantation of the device and/or any invasive or noninvasive stimulation of the vagus nerve. In other embodiments, the test involves activating the cholinergic anti-inflammatory pathway for a short duration using techniques that are either non-invasive or minimally invasive as described herein. For example, the vagus nerve can be stimulated electrically or mechanically, as described herein. The extent of the patient's biological response to temporary CAP activation may then be assessed by measuring pathway-mediated inhibition of immune activation in assays performed on blood samples or other biological fluids taken before and after the stimulation. Surprisingly, the extent of the patient's biological response to a brief non- or minimally invasive (e.g., acutely invasive) activation of the pathway can predict clinical response to the permanent implant.

Activation of the cholinergic anti-inflammatory pathway may be achieved through any of the following stimulation techniques: (1) noninvasive transcutaneous stimulation of the auricular branch of the vagus nerve which innervates the skin of the cymba conchae of the ear, using either electrical or mechanical stimulation; (2) stimulation of the cervical vagus nerve using a catheter-directed temporary electrical lead/electrode, introduced intravascularly via percutaneous puncture, and positioned within the cervical internal jugular vein or other nearby vein under fluoroscopic or ultrasound guidance to place it in close apposition to the cervical portion of the vagus nerve; (3) stimulation of the cervical vagus nerve by a temporary catheter-directed non-cuffed electrical lead/electrode, introduced into the carotid sheath by percutaneous puncture, and positioned under fluoroscopic, ultrasound, and/or endoscopic guidance to place it in close apposition to the cervical portion of the vagus nerve within the carotid sheath; (4) stimulation of the cervical vagus nerve by trans-vascular mechanical pressure using an intravascular angioplasty balloon or other expandable element, introduced via percutaneous puncture and positioned under fluoroscopic or ultrasound guidance in close apposition to the cervical portion of the vagus nerve within the cervical internal jugular vein or other nearby vein; and (5) noninvasive transcutaneous cervical vagus nerve stimulation using a transcutaneous electrical nerve stimulation device placed over the vagus nerve on the skin of the patient's neck.

Assessment of the strength of CAP activation can measured using the change from pre- to post stimulation levels in any of the following parameters in a tissue sample or biological fluid such as whole blood, serum, or supernatants from cultures of whole blood, or from cells isolated from whole blood: (1) cytokines or inflammatory mediators or other analytes; and (2) reduction in inducible release of cytokines or other inflammatory mediators or other analytes, from in vitro culture of whole blood or isolated cells from blood. Such induction may be in the form of bacterial lipopolysaccharide, other Toll-like receptor activators, fragments of complement molecules (e.g., C5a), or activating antibodies directed against T cell or B cell surface receptors (e.g. anti CD3/anti CD28 antibodies).

Alternative Stimulation Locations

Other regions of the subject's body may be alternatively or additionally stimulated, particularly regions enervated by nerves of the inflammatory reflex. For example, the non-invasive stimulation and other stimulation modalities described herein may be applied to the subject's area innervated by the seventh (facial) cranial nerve or cranial nerve V. The non-invasive stimulation and other stimulation modalities described herein may be applied to at least one location selected from: the subject's cymba conchae of the ear, or helix of the ear. In some variations, the non-invasive stimulation and other stimulation modalities described herein is applied to at least one point along the spleen meridian.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims. The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of treating a patient having an inflammatory disorder with vagus nerve stimulation, the method comprising:
    challenging a first sample of blood with a first concentration of a toxin, wherein the first sample is taken from the patient prior to implantation of a vagus nerve stimulator;
    challenging a second sample of blood with a second concentration of the toxin that is at least 2 times the first concentration, wherein the second sample is taken from the patient prior to implantation of the vagus nerve stimulator; and
    implanting the vagus nerve stimulator to treat the patient for the inflammatory disorder when an amount of an inflammatory cytokine released in response to the second concentration of the toxin is greater than an amount of the inflammatory cytokine released in response to the first concentration of the toxin by a threshold.

2. The method of claim 1, wherein implanting comprises implanting the vagus nerve stimulator to treat the patient for the inflammatory disorder when a ratio of the amount of the inflammatory cytokine released in response to the second concentration of the toxin and the amount of the inflammatory cytokine released in response to the first concentration of the toxin is greater than a threshold ratio.

3. The method of claim 2, wherein the threshold ratio is greater than 60.

4. The method of claim 1, further comprising determining a ratio of a measure of the amount of the inflammatory cytokine released in response to the second concentration of the toxin and the amount of the inflammatory cytokine released in response to the first concentration of the toxin.

5. The method of claim 4, further comprising displaying an indication that the patient is a responder or a non-responder based on the amount of the inflammatory cytokine released in response to the second concentration of the toxin compared to the amount of the inflammatory cytokine released in response to the first concentration of the toxin.

6. The method of claim 1, further comprising measuring the amount of the inflammatory cytokine that is released in response to the first concentration and measuring the amount of the inflammatory cytokine that is released in response to the second concentration.

7. The method of claim 1, wherein the toxin is an endotoxin.

8. The method of claim 1, wherein the toxin is a Lipopolysaccharide (LPS).

9. The method of claim 1, further comprising challenging a third sample of blood with a third concentration of the toxin that is at least 2 times the second concentration, wherein the third sample is taken from the patient prior to stimulation of the patient's vagus nerve and wherein implanting the vagus nerve stimulator comprises implanting the vagus nerve stimulator when an amount of an inflammatory cytokine released in response to the third concentration of the toxin is greater than an amount of the inflammatory cytokine released in response to the first and second concentrations of the toxin by the threshold.

10. The method of claim 1, wherein challenging the second sample of blood with the toxin at the second concentration comprises challenging with a concentration that is at least 10 times the first concentration.

11. The method of claim 1, wherein the first sample of blood and the second sample of blood are portions of a master sample taken from the patient.

12. The method of claim 1, wherein the inflammatory cytokine is one or more of: TNF, IL-1, IL-6, IL-12, IL-18, inflammsome, interferon gamma, and granulocyte-macrophage colony stimulating factor.

* * * * *